United States Patent [19]
Cushman et al.

[11] Patent Number: 5,553,714
[45] Date of Patent: Sep. 10, 1996

[54] METHOD FOR DETECTING AND SEPARATING THERMOPLASTIC CONTAINERS WITH NEAR INFRARED FLUOROSPHORES

[75] Inventors: Michael R. Cushman; James J. Krutak; William W. Parham; Clarence A. Coates; Max A. Weaver, all of Kingsport, Tenn.; Gabor Patonay, Stone Mountain, Ga.

[73] Assignee: Eastman Chemical Company, Kingsport, Tenn.

[21] Appl. No.: 339,318

[22] Filed: Nov. 14, 1994

Related U.S. Application Data

[63] Continuation of Ser. No. 789,570, Nov. 8, 1991, abandoned.

[51] Int. Cl.$^6$ ............................... B07C 5/10; C08K 5/34
[52] U.S. Cl. ........................ 209/577; 209/3.3; 209/576; 524/87; 524/88
[58] Field of Search ................................. 209/576, 577, 209/3.3, 4; 524/87–89, 174

[56] References Cited

U.S. PATENT DOCUMENTS

| | | | |
|---|---|---|---|
| 3,207,910 | 9/1965 | Hirschfeld et al. | 209/577 |
| 3,630,941 | 12/1971 | Bergmark | 252/186 |
| 4,250,078 | 2/1981 | McFarlane et al. | 260/40 R |
| 4,321,133 | 3/1982 | DiGiacomo | 209/3.3 |
| 4,408,004 | 10/1983 | Pengilly | 524/398 |
| 4,420,581 | 12/1983 | McFarlane et al. | 524/431 |
| 4,423,814 | 1/1984 | White | 209/3.3 |
| 4,476,272 | 10/1984 | Pengilly | 524/398 |
| 4,535,118 | 8/1985 | Pengilly | 524/398 |
| 4,540,595 | 9/1985 | Acitelli et al. | 427/7 |
| 4,541,438 | 9/1985 | Parker et al. | 128/664 |
| 4,606,859 | 8/1986 | Duggan et al. | 540/122 |
| 4,816,386 | 3/1989 | Gotoh | 524/88 |
| 4,904,567 | 2/1990 | Maeda et al. | 430/270 |
| 4,915,827 | 4/1990 | Rosenthal | 209/577 |
| 4,981,888 | 1/1991 | Langley et al. | 524/88 |
| 4,983,817 | 1/1991 | Dolach et al. | 235/462 |
| 4,992,204 | 2/1991 | Kluger et al. | 252/301.16 |
| 5,093,147 | 3/1992 | Andrus et al. | 427/7 |
| 5,102,980 | 4/1992 | Krutak et al. | 524/88 |
| 5,201,921 | 4/1993 | Luttermann et al. | 8/506 |

FOREIGN PATENT DOCUMENTS

| | | |
|---|---|---|
| 331876 | 9/1989 | European Pat. Off. . |
| 427535 | 5/1991 | European Pat. Off. . |
| 227520 | 9/1985 | Germany . |
| 4024130A1 | 7/1990 | Germany . |
| 1537375 | 12/1978 | United Kingdom . |
| 2158833 | 11/1985 | United Kingdom . |
| 2168372 | 6/1986 | United Kingdom . |

OTHER PUBLICATIONS

Abstract of U.S.P. 5039600 and U.S.P. 5034309, both issued to Tai et al.
Chemical Abstract vol. 114: 196444n.
Japanese Patent Application No. 143346 (Jun. 6, 1989).
Japanese Patent Application No. 215639 (Abstract only).
Chemical Abstract vol. 77: 141469.
Chemical Abstract vol. 114: 230681z.
Chemical Abstract vol. 114: 230682a
R & D Magazine, Jul. 1990, p. 102.
Analytical Chemistry, vol. 63, No. 6, 1991, pp. 321–327.
Great Britain Application 25282 (Nov. 9, 1989).
Japanese Application 209237 (Mar. 27, 1991).
J.A.C.S., 106, pp.7404–7410, (1984).
Chemical Abstract vol. 106: 86223s (Jap. Patent Application No. 61,215,663).
Chemical Abstract vol. 114: 196445p (Jap. Patent Application No. 02,276,678).
Chemical Abstract vol. 114: 196418g (Japanese Patent Application No. 90,187,391).

*Primary Examiner*—Tae Yoon
*Attorney, Agent, or Firm*—Karen A. Harding; Harry J. Gwinnell

[57] ABSTRACT

Provided is a method for tagging thermoplastic containers using near infrared fluorescing compounds or copolymerized residues readily capable of detection. Also provided is a method for identifying a thermoplastic container. Also provided are thermoplastic polymer compositions comprised of the near infrared fluorescing compounds or residues and articles comprised of such compositions.

1 Claim, 2 Drawing Sheets

METHOD FOR DETECTING AND SEPARATING THERMOPLASTIC CONTAINERS WITH NEAR INFRARED FLUOROSPHORES

This is a continuation of Ser. No. 07/789,570, filed on Nov. 8, 1991, now abandoned.

FIELD OF THE INVENTION

The present invention belongs to the field of polymer chemistry. More particularly, this invention relates to a method for tagging thermoplastic polymers in order to allow for their differentiation and physical sorting.

BACKGROUND OF THE INVENTION

Billions of pounds of thermoplastic polymers are used annually in the world for producing fibers, films, shaped articles, bottles, etc. Disposal of these polymeric materials by incineration or by placing them in land fills is becoming unacceptable due largely to the ever-increasing environmental impact. Recycling offers many advantages from an environmental standpoint; however, efforts so far have been hampered by the lack of fast, convenient, and economically attractive methods for identification and separation (sorting) of the various thermoplastic polymers currently available in the marketplace, and hence ending up in landfills. It has been estimated that plastics comprise 7.3 percent by weight of all municipal solid waste, of which only about 1 percent is currently recycled (U.S. Congress, Office of Technology Assessment "Facing America's Trash: What Next for Municipal Solid Waste", OTA-O-424 (Washington, D.C.; U.S. Government Printing Office, October, 1989)). Visual identification and manual separation techniques presently used for sorting and separation of plastics are labor intensive and expensive in addition to being subject to human error. Efforts to use some inherent physical property of the plastics such as density for identification and separation have thus far not proven to be attractive. To allow plastics to become truly recyclable, plastic compositions which have unique properties which allow them to be separated from each other by automated methods, as opposed to manual separation, are thus very desirable.

It is known (U.S. Pat. No. 4,540,595) that one may mark documents such as bank checks by the use of inks that fluoresce in the near infrared region, i.e., generally between 650 and 800 nm, for automatic identification. Fluorescent phenoxazine dyes of the formula

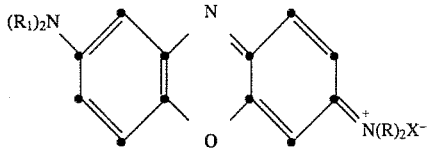

wherein $R_1$ and R are alkyl and $X^-$ is an anion are shown to be effective near-infrared fluorescing compounds for this purpose. Attempts to use these compounds for adding to thermoplastics to impart fluorescence in the near infrared have failed because the high temperatures necessary for the preparation and processing of thermoplastics cause decomposition of the phenoxazine compounds.

A method for separation of magnesium bearing ore particles based on the presence of a fluorescent compound, i.e., 8-hydroxyquinoline, is known (U.S. Pat. No. 4,423,814). The conditioned ore is irradiated with UV light to induce fluorescence and the magnesium-rich mineral separated from the lean ore particles by detecting the difference of the fluorescence intensity. This method of identification and sorting, based on the use of compounds which fluoresce in the UV light range is not appropriate for thermoplastics in general because many absorb UV light themselves as well as the absorbance by residual products packaged therein. U.S. Pat. No. 4,321,133 discloses a similar process for sorting limestone ores.

A method for sorting agricultural materials based on irradiation with near-infrared light has also been disclosed (U.S. Pat. No. 4,915,827). Absorption in the infrared region is measured and compared to predetermined infrared absorption criteria, which criteria distinguish the desired material from undesired material. This method does not relate to plastic materials and does not involve near infrared fluorescence as a distinguishing part of the method.

Near infrared absorbing compounds such as carbon black (U.S. Pat. Nos. 4,408,004; 4,476,272; 4,535,118) and iron oxide ($Fe_2O_3$) (U.S. Pat. Nos. 4,250,078; 4,420,581) have been added to thermoplastic polyesters in small quantities to improve heat-up rates during molding operations. These near infrared light absorbing compounds are not fluorescent and thus cannot be used as near infrared fluorescing "tags".

Further, it has been proposed that one may separate polyvinyl chloride bottles from polyester bottles based on an x-ray method (R&D Magazine, July 1990, p. 102). The x-ray detector is sensitive to the chlorine found in polyvinyl chloride plastics, but not sensitive to the polyester plastics since they contain no chlorine. Obviously, this separation method is very limited in applicability and involves the use of hazardous x-ray radiation.

Near infrared fluorescing compounds have also been used in immunoassay procedures for identifying cancerous tissue in the human body (U.S. Pat. No. 4,541,438).

Finally, it has been proposed (G. Patonay, Analytical Chemistry, Vol. 63, No. 6, 1991, pp 321–327) to use near infrared fluorescent compounds for fluorogenic labels for biomolecules; however, the disclosed fluorescent compounds have poor thermal stability and are not suitable for tagging or marking thermoplastic compositions.

SUMMARY OF THE INVENTION

This invention relates to a method for "marking" or "tagging" a thermoplastic polymeric material by incorporating one or more thermally stable, near infrared fluorescing compounds therein by admixing or copolymerizing or by blending with certain condensation polymers containing one or more near infrared fluorescing compounds copolymerized or admixed therein and a method for separating or sorting a mixture of thermoplastic containers such as bottles. Also provided are thermoplastic polymer compositions tagged with such compounds or residues.

BRIEF DESCRIPTION OF THE DRAWINGS

FIGS. 1 and 2 are more fully described below.

DETAILED DESCRIPTION OF THE INVENTION

Figure 1:
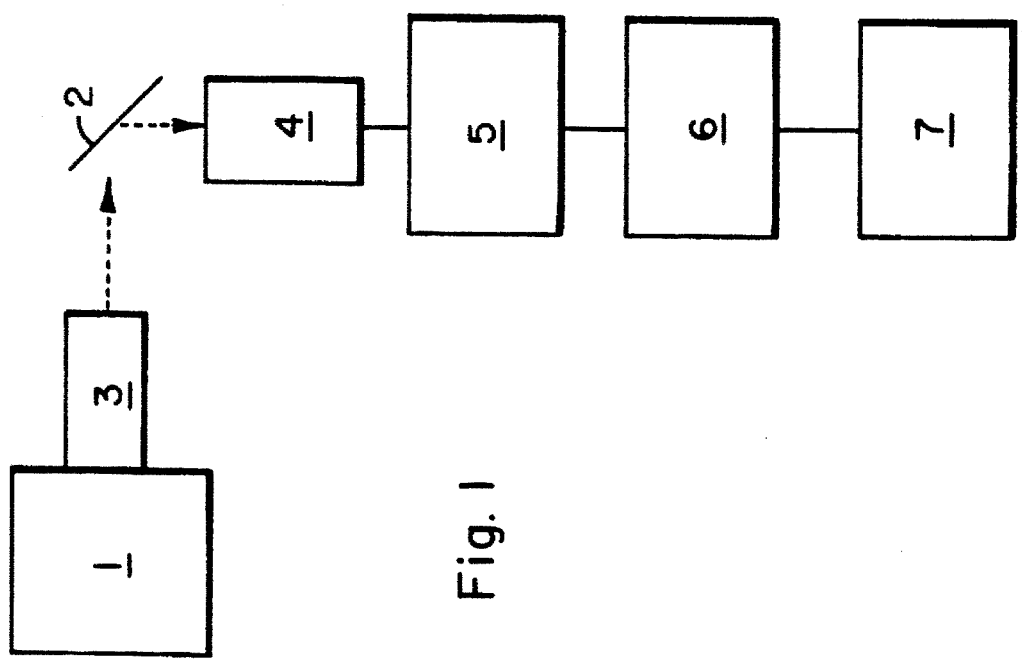
FIG. 1 depicts an apparatus useful for practicing the present invention for identification of the near infrared (NIR) marker in the polymer described herein. This arrangement will be understood to be an application of commercially available fluorometers. As may be seen from FIG. 1, there is present a light source (1) capable of emitting radiation in the visible and NIR region which illuminates the polymer sample (2) through a wavelength selector (3) e.g., monochromator or interference filter. A wavelength selector (4) and a NIR sensitive photodetector (5) is placed at 90° or less angle. It may be seen from FIG. 1 that light source (1), wavelength selector (3 & 4) and photodetector (5) are all arranged on two sides of a triangle to minimize scattered light entering the detector. The light source (1) in FIG. 1 may be replaced with lasers, preferably semiconductor lasers. The output of photodetector (5) is provided to level adjustment amplifier (6), the output of which is provided to an integrated circuit digital multimeter (7). The output of the digital multimeter is connected to a computer display so as to provide a numeral and graphical indication of the amount of luminous flux at the predetermined wavelength (preferably at the emission maxima) emitted by the substance contained in polymer.

This invention provides a method for "tagging" for identification purposes one or a mixture of thermoplastic polymers comprising contacting said polymers with one or a mixture of thermally stable, near infrared fluorescent tagging compounds, wherein said tagging compound has substantial near infrared radiation absorbance and is added in sufficient quantity to impart fluorescence capable of detection by a near infrared radiation detector when exposed to electromagnetic radiation having wavelengths of about 670–2500 nm.

Another embodiment of the invention relates to a method for "tagging" a condensation polymer such as a polyester or polycarbonate material comprising copolymerizing one or a mixture of thermally stable, near infrared fluorescent tagging compounds therein during said polymer preparation, wherein the tagging compound(s) has (have) substantial near infrared radiation absorbance and is added in sufficient quantity to impart fluorescence capable of detection by a near infrared radiation detector when exposed to electromagnetic radiation having wavelengths of about 670–2500 nm.

A further embodiment of the invention relates to a method for "tagging" a thermoplastic polymer material comprising having the same with a condensation polymer selected from polyesters, polycarbonates and polyurethanes containing at least 10 ppm of one or more thermally stable, near infrared fluorescent compounds copolymerized therein, said "tagging" compound being present in the final thermoplastic polymeric composition in sufficient quantity to impart fluorescence capable of detection by a near infrared radiation detector when exposed to electromagnetic radiation having wavelengths of about 670–2500 nm.

This invention also relates to a method for detecting and separating thermoplastic containers by polymer type, said containers comprising a thermoplastic material containing a compound or residue having detectible fluorescence when exposed to near infrared radiation, which comprises the following steps:

(a) exposure of a mixture of thermoplastic containers to near infrared radiation having wavelengths of about 670–2500 nm, with the provision that at least one of said thermoplastic container compositions contain one or more near infrared tagging compounds or residues having near infrared absorbance and which is (are) present in sufficient quantity to impart fluorescence when exposed to radiation having wavelengths of about 670–2500 nm, provided by light sources;

(b) detection of the emitted (fluorescent) light via near infrared light detection means; and (c) separating the fluorescing containers from the non-fluorescing containers or containers fluorescing at a detectibly different wavelength or wavelengths by mechanical means.

In the above method, it will be appreciated that near infrared detection means denotes any apparatus capable of detecting fluorescence in the range described herein. Such detection means are the devices for detecting photons emitted by the fluorescent containers at wavelengths of about 670 to 2500nm such as photomultiplier tubes, solid state detectors, semiconductor based detectors, or any such device. The preferred means of detection has an optimum sensitivity at the preferred wavelength region. Examples include the silicon photodiodes or germanium detectors.

The term "light sources" refers to devices used to irradiate the samples with near infrared radiation having wavelength outputs from 670 to 2500nm such as laser diodes, solid state lasers, dye lasers, incandescent, or any other known light source. Such light sources can be used in conjunction with wavelength selectors such as filters, monochromators, etc. The preferred light sources are those that have a maximum signal at the maximum of the absorbance of the tagging fluorophore. Examples include the laser diodes, light emitting diodes, or solid state lasers.

In the above method, the phrase "detectibly different wavelength or wavelengths" refers to phenomenon that fluorescence by one or more of the near infrared fluorophores will occur at a different wavelength (or wavelengths in the case of >1 fluorophores) and such difference will, by necessity be one that is capable of detection. Using state of the art detection equipment it is believed that such differences in absorption/fluorescence of as little as 20 nm in wavelength can be discerned. Of course, this limitation is not critical and will decrease as detection methodology improves.

The presence of a near infrared fluorophore (NIRF) provides highly effective tags for identification of thermoplastics. Since most polymers themselves absorb UV light, and if they are colored also absorb visible light, "tagging" or "marking" components based on fluorescent UV and/or visible light absorbing compounds are not practical; however, interference from the thermoplastics themselves or from typical additives present therein or from typical contamination present thereon is minimal in the near infrared region of the electromagnetic spectrum, thus allowing the NIRF "tag" to be detected in the presence of a complex matrix, while being largely "invisible". This permits design of an automated separation system which operates with zero or few false positive identifications and at very high speeds, e.g., greater than 3000 lb./hour.

Ideally, for the practice of this invention the NIRF "tag" should have excellent thermal stability and little light absorption in the visible region; that is, they should impart little or no color to the thermoplastic polymer to which the NIRF is copolymerized or admixed with. Also, they should have strong absorption of near infrared light (high molar extinction coefficients, e.g. >20,000) and have strong fluorescence in the near infrared over the wavelengths of about 670–2500 nm. Suitable stability to sunlight and fluorescent light and low extractability or sublimation from the thermoplastic compositions are also preferred. To produce essentially "invisible" tags the near infrared fluorescent compounds must absorb little if any light having wavelengths in the 400–700 nm range; however, since the compounds are present in extremely low concentrations, a small amount of absorption may be tolerated without imparting significant color.

It is within the scope of this invention to mark one or more different thermoplastic compositions with one or more near infrared fluorescing compounds and to identify and separate containers derived therefrom based on the fact that the near infrared fluorescing compounds can be selected such that they absorb infrared light and reemit fluorescent light at wavelengths different enough from each other as not to interfere with individual detection.

Thus, the present invention also provides a thermoplastic polymer composition which comprises a thermoplastic polymer having admixed therein one or more near-infrared fluorescing compounds, provided that said near-infrared flourescing compounds do not substantially absorb light in the visible spectrum, wherein said compounds are present in a concentration sufficient to impart fluorescence capable of detection by near infrared detection means when exposed to electromagnetic radiation having a wavelength of about 670 to 2500 nm.

As a further aspect of the present invention, there is provided a thermoplastic polymer composition which comprises a thermoplastic condensation polymer having copolymerized therein at least 0.01 ppm (parts per million) of one or more near infrared flourescing compounds.

As a further aspect fo the present invention, there is porvided a shaped or formed article comprised of the tagged thermoplastic polymer compositions disclosed herein. It is within the scope of this invention for said compositions to have NIRF compounds admixed therein, coated thereon, or copolymerized therein.

Some of the compounds useful in the practice of this invention are known (U.S. Pat. Nos. 4,606,859; 4,904,567; 5,034,309; and 5,039,600, incorporated herein by reference; UK Pat. 1,537,375; UK Pat. Appl. GB 2,168,372; JACS, 1984, 106, pp 7404–7410; Jap. Pat. 61,215,663 (CA Vol. 106: 86223s); Jap. Pat. 02,276,676 (CA Vol. 114: 196445p); Jap. Pat. 02,187,391 (CA Vol. 114: 196418g); however, such compounds are taught to be useful for infrared inks, liquid crystal displays, optical recording devices, electrochemical chemiluminescence and as colorants. No mention is made of the use of these compounds as NIR(near infrared) fluorescent (or NIRF) "tags" for marking thermoplastics for identification and separation.

The preferred near infrared fluorescent compounds useful in the practice of the invention are selected from the classes of phthalocyanines, naphthalocyanines and squaraines (derivatives of squaric acid) and correspond to Formulae II, III and IV:

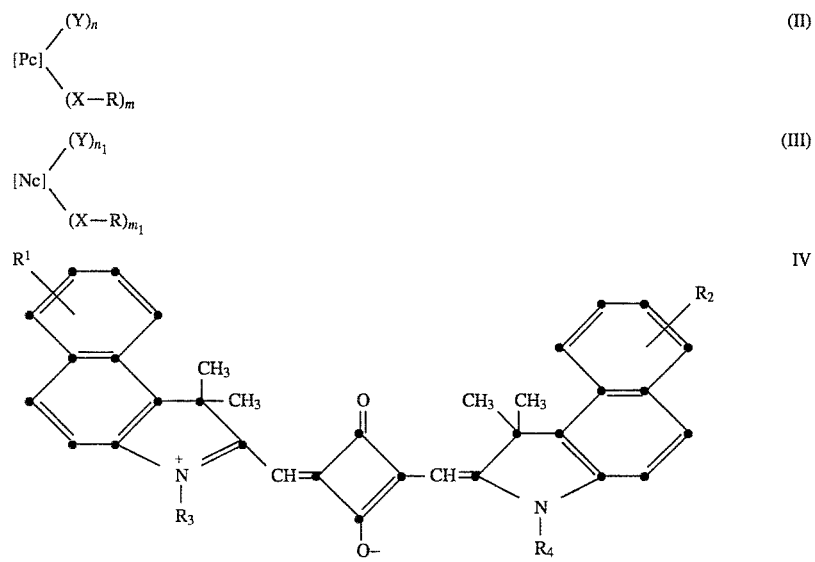

wherein Pc and Nc represent the phthalocyanine and naphthalocyanine moieties of Formulae IIa and IIIa, Phthalocyanine

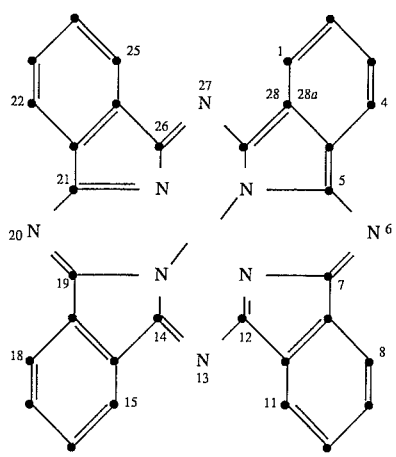

2,3-Naphthalocyanine

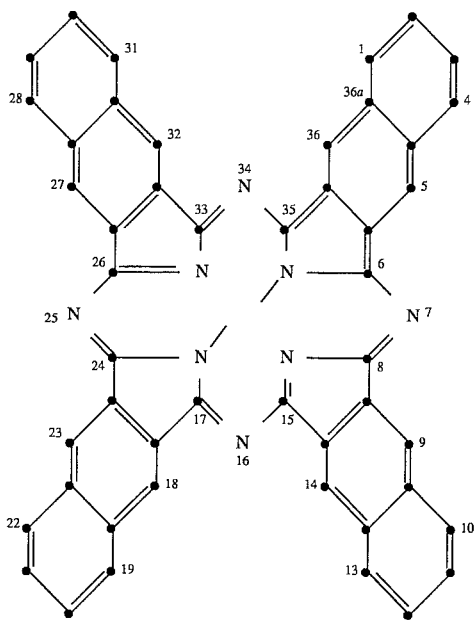

respectively, covalently bonded to hydrogen or to various metals, halometals, organometallic groups, and oxymetals including AlCl, AlBr, AlF, AlOH, $AlOR_5$, $AlSR_5$, Ca, Co, CrF, Cu, Fe, Ge, $Ge(OR_6)$, Ga, InCl, Mg, Mn, Ni, Pb, Pt, Pd, $SiCl_2$, $SiF_2$, $SnCl_2$, $Sn(OR_6)_2$, $Si(OR_6)_2$, $Sn(SR_6)_2$, $Si(SR_6)_2$, Sn, TiO, VO or Zn, wherein $R_5$ and $R_6$ are selected from hydrogen, alkyl, aryl, heteroaryl, lower alkanoyl, trifluoroacetyl, groups of the formulae

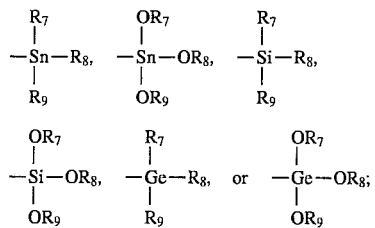

$R_7$, $R_8$ and $R_9$ are independently selected from alkyl, phenyl or phenyl substituted with lower alkyl, lower alkoxy or halogen;

X is selected from oxygen, sulfur, selenium, tellurium or a group of the formula $N-R_{10}$, wherein $R_{10}$ is hydrogen, cycloalkyl, alkyl, acyl, alkylsulfonyl, or aryl or $R_{10}$ and R taken together form an aliphatic or aromatic ring with the nitrogen atom to which they are attached;

Y is selected from alkyl, halogen or hydrogen;

R is selected from unsubstituted or substituted alkyl, alkenyl, alkynyl, $C_3$-$C_8$ cycloalkyl, aryl, heteroaryl,

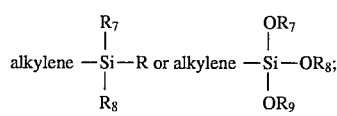

or $-(X-R)_m$ is alkylsulfonylamino, arylsulfonylamino, or a group selected from the formulae $-X(C_2H_4O)_zR^1$,

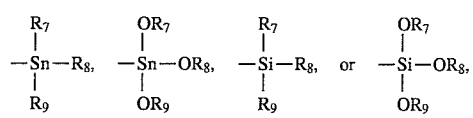

wherein $R^1$ is hydrogen or R as defined above; Z is an integer of from 1–4; or two $-(X-R)_m$ groups can be taken together to form divalent substituents of the formula

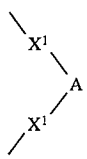

wherein each $X^1$ is independently selected from $-O-$, $-S-$, or $-N-R_{10}$ and A is selected from ethylene; propylene; trimethylene; and such groups substituted with $C_1$-$C_4$ alkyl, $C_1$-$C_4$ alkoxy, aryl and cycloalkyl; 1,2-phenylene and 1,2-phenylene containing 1–3 substituents selected from $C_1$-$C_4$ alkyl, $C_1$-$C_4$ alkoxy or halogen;

$R_1$ and $R_2$ are independently selected from hydrogen, lower alkyl, lower alkoxy, halogen, aryloxy, lower alkylthio, arylthio, lower alkylsulfonyl, arylsulfonyl; lower alkylsulfonylamino, arylsulfonylamino, cycloalkylsulfonylamino, carboxy, unsubstituted and substituted carbamoyl and sulfamoyl, lower alkoxycarbonyl, hydroxy, lower alkanoyloxy,

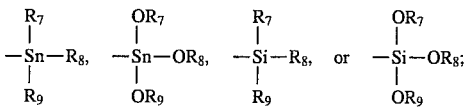

$R_3$ and $R_4$ are independently selected from hydrogen, lower alkyl, alkenyl or aryl; n is an integer from 0–12; $n_1$ is an integer from 0–16, m is an integer from 4–16; $m_1$ is an integer from 0–16; provided that the sums of n+m and $n_1+m_1$ are 16 and 24, respectively.

In a preferred embodiment of this aspect of the present invention m is from 4 to 12; $m_1$ is from 0–8; provided that in the definitions of the substituents $(Y)n$, $(Y)n_1$ and $(-X-R)m_1$ that these substituents are not present when n, $n_1$ and $m_1$ are zero, respectively. Substituents $(X-R)m$ and $(Y)n$ are present in compounds IIa on the peripheral carbon atoms, i.e. in positions 1, 2, 3, 4, 8, 9, 10, 11, 15, 16, 17, 18, 22, 23, 24, 25 and substituents $(X-R)m_1$ and $(Y)n_1$ are present on the peripheral carbon atoms of III, i.e. in positions 1, 2, 3, 4, 5, 9, 10, 11, 12, 13, 14, 18, 19, 20, 21, 22, 23, 27, 28, 29, 30, 31, 32 and 36.

In the above definitions, the term alkyl is used to designate a straight or branched chained hydrocarbon radical containing 1–12 carbons.

In the terms lower alkyl, lower alkoxy, lower alkylthio, lower alkoxycarbonyl, lower alkanoyl and lower alkanoyloxy the alkyl portion of the groups contains 1–6 carbons and may contain a straight or branched chain.

The term "cycloalkyl" is used to represent a cyclic aliphatic hydrocarbon radical containing 3–8 carbons, preferably 5 to 7 carbons.

The alkyl and lower alkyl portions of the previously defined groups may contain as further substituents one or more groups selected from hydroxy, halogen, carboxy, cyano, $C_1$–$C_4$-alkoxy, aryl, $C_1$–$C_4$-alkylthio, arylthio, aryloxy, $C_1$–$C_4$-alkoxycarbonyl or $C_1$–$C_4$-alkanoyloxy.

The term "aryl" includes carbocyclic aromatic radicals containing 6–18 carbons, preferably phenyl and naphthyl, and such radicals substituted with one or more substituents selected from lower alkyl, lower alkoxy, halogen, lower alkylthio, N(lower alkyl)$_2$, trifluromethyl, carboxy, lower alkoxycarbonyl, hydroxy, lower alkanoylamino, lower alkylsulfonylamino, arylsulfonylamino, cycloalkylsulfonylamino, lower alkanoyloxy, cyano, phenyl, phenylthio and phenoxy.

The term "heteroaryl" is used to represent mono or bicyclic hetero aromatic radicals containing at least one "hetero" atom selected from oxygen, sulfur and nitrogen or a combination of these atoms. Examples of suitable heteroaryl groups include: thiazolyl, benzothiazolyl, pyrazolyl, pyrrolyl, thienyl, furyl, thiadiazolyl, oxadiazolyl, benzoxazolyl, benzimidazolyl, pyridyl, pyrimidinyl and triazolyl. These heteroaryl radicals may contain the same substituents listed above as possible substituents for the aryl radicals. The term triazolyl also includes structure V and mixed isomers thereof,

wherein $R_{11}$ is hydrogen or selected from lower alkyl and lower alkyl substituted with one or two groups selected from hydroxy, halogen, carboxy, lower alkoxy, aryl, cyano, cycloalkyl, lower alkanoyloxy or lower alkoxycarbonyl.

The terms "alkenyl and alkynyl" are used to denote aliphatic hydrocarbon moiety having 3–8 carbons and containing at least one carbon-carbon double bond and one carbon-carbon triple bond, respectively.

The term halogen is used to include bromine, chlorine, fluorine and iodine.

The term "substituted alkyl" is used to denote a straight or branched chain hydrocarbon radical containing 1–12 carbon atoms and containing as substituents 1 or 2 groups selected from hydroxy, halogen, carboxy, cyano, $C_1$–$C_4$ alkoxy, aryl, $C_1$–$C_4$ alkylthio, arylthio, aryloxy, $C_1$–$C_4$ alkoxycarbonyl, or $C_1$–$C_4$ alkanoyloxy.

The term "substituted carbamoyl" is used to denote a radical having the formula —CONR$_{12}$R$_{13}$, wherein R$_{12}$ and R$_{13}$ are selected from unsubstituted or substituted alkyl, alkenyl, alkynyl, cycloalkyl, aryl, or heteroaryl.

The term "substituted sulfamoyl" is used to denote a radical having the formula —SO$_2$NR$_{12}$R$_{13}$, wherein R$_{12}$ and R$_{13}$ are as defined above.

The term "alkylene" refers to a divalent $C_1$–$C_{12}$ aliphatic hydrocarbon moiety, either straight or branched-chain, and either unsubstituted or substituted with one or more groups selected from lower alkoxy, halogen, aryl, or aryloxy.

The term "acyl" refers to a group of the formula R$^o$C(O)—O—, wherein R$^o$ is preferably a $C_1$–$C_{10}$ alkyl moiety. The term "alkyl sulfonyl" refers to a group of the formula R$^o$SO$_2$—, wherein R$^o$ is as defined for acyl.

Preferred —X—R groups include those listed in Table I.

As noted above, the near infrared fluorescing compounds having reactive groups present may be copolymerized to produce thermoplastic compositions such as polyesters or polycarbonates containing the fluorophore covalently bound so that they will not be leachable, sublimable, extractable, or be exuded from the polymer composition. This feature is particularly desireable for thermoplastic polymers used for containers for comestibles such as beverages and food.

Thus, in a preferred embodiment of the invention there is provided a molding grade polyester, polyurethane, or polycarbonate condensation polymer having copolymerized therein a total of from about 0.1 ppm to 100 ppm of at least one thermally stable, near infrared fluorescing compound of Formulae II, III or IV above containing at least one reactive functional group, said group selected from hydroxy, carboxy or an ester radical having the formulae

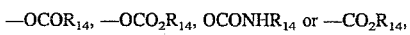

—OCOR$_{14}$, —OCO$_2$R$_{14}$, OCONHR$_{14}$ or —CO$_2$R$_{14}$, wherein R$_{14}$ is selected from unsubstituted or substituted alkyl, cycloalkyl or aryl radicals. R$_{14}$ preferably is unsubstituted alkyl, e.g., alkyl of up to about 8 carbons, or phenyl, and most preferably lower alkyl, e.g., methyl and ethyl. The reactive group preferably is hydroxy, carboxy, carbomethoxy, carbethoxy or acetoxy. The compounds normally contain 1 to about 8 reactive groups, preferably 2. Of course, when only one reactive groups is present, chain termination may occur during reaction and when more than 2 reactive groups are present cross-linking occurs; however, when the near infrared fluorescing compounds are added at the extremely low levels needed to impart a detectable amount of fluorescence they do not significantly interfere with the polycondensation reaction.

In a further aspect of the invention, there is provided amorphous and partially crystalline polyesters containing at least one thermally stable, near infrared fluorescing compound, preferably a compound having the Formulae II, III or IV above, and containing two reactive groups copolymerized therein at a level of greater than 10 ppm to about 30.0 weight percent. The preferred level of the fluorophore percent is about 0.1 to about 10.0 weight present. This "concentrate" composition containing the copolymerized "tagging" compound can be obtained as a powder or in pellet form and can be admixed with polyester or another thermoplastic polymer to provide a suitably "tagged" composition mentioned earlier. Such blends represent a further embodiment of the present invention.

The useful types of polyesters of this invention are linear, thermoplastic, crystalline or amorphous and have one or more near infrared fluorescing compounds, preferably of Formulae II, III or IV above copolymerized therein.

The diol components of the polyester may be comprised of, for example, ethylene glycol, 1,4-cyclohexanedimethanol, 1,2-propanediol, 1,3-propanediol, 2-methyl-1,3-propanediol, 1,6-hexanediol, 1,2-cyclohexanediol, 1,4-cyclohexanediol, 1,10-decanediol, 1,2-cyclohexanedimethanol, 1,3-cyclohexanedimethanol, X,8-bis-(hydroxymethyl)-tricyclo- [5.2.1.0]-decane wherein X represents 3, 4, or 5; and diols containing one or more oxygen atoms in the chain, e.g., diethylene glycol, triethylene glycol, dipropylene glycol, or tripropylene glycol and the like. In general, these diols contain 2 to 18, preferably 2 to 12 carbon atoms. Cycloaliphatic diols can be employed in their cis or trans configuration or as a mixture of both forms.

The acid components (aliphatic, alicyclic, or aromatic dicarboxylic acids) of the polyester may consist of, for example, terephthalic acid, naphthalene 2,6-dicarboxylic acid, isophthalic acid, 1,4-cyclohexanedicarboxylic acid, 1,3-cyclohexane dicarboxylic acid, succinic acid, glutaric acid, adipic acid, sebacic acid, 1,12-dodecanedioic acid, and the like. In place of the dicarboxylic acids themselves, it is possible and often preferable to use a functional acid derivative thereof such as the dimethyl, diethyl, or dipropyl ester of the dicarboxylic acid. The anhydrides of the dicarboxylic acids can likewise be employed.

The polyesters can be produced using typical polycondensation techniques well known in the art.

Typical polycarbonates useful in the practice of the invention are disclosed in Kirk-Othmer Encyclopedia of Chemical Technology, third edition, Vol. 18, pp 479–494.

A wide range of thermoplastic polymers suitable for blending with the above condensation polymers (which contain the NIRF(s)) is known in the art and includes polyesters e.g., poly(ethylene terephthalate) and poly(butylene terephthalate); polyolefins, e.g., polypropylene, polyethylene, linear low density polyethylene, polybutylene and copolymers made from ethylene, propylene and/or butylene; polyamides, e.g., nylon 6 and nylon 66; polyvinyl chloride; polyvinylidene chloride; polycarbonates; cellulose esters, e.g., cellulose acetate, propionate, butyrate or mixed esters; polyacrylates, e.g., poly(methyl methacrylate); polyimides; polyester-amides; polystyrene; ABS (acrylonitrile-butadiene-styrene) type polymers, and (TPO) thermoplastic oligomers, etc.

In the practice of one aspect of the invention the NIR fluorophores are incorporated into the thermoplastic resins using conventional techniques such as those employed to incorporate other additives in such resins (see R. Gächter and H. Müeller, Editors, Plastics Additives Handbook, Hansu Publishers, New York, 1985, pp 507–533; 729–741). For example, the NIR fluorophores may be dry blended in the form of powders with the thermoplastic materials in the form of pellets or powders, with or without an adhesion promoter or a dispersing agent. This premix can be subsequently processed on extruders or molding machines. In some cases, solution blending may also be preferable. Of course, other conventional additives such as plasticizers, antioxidants, stablizziers, nucleating agents, etc., may also be present in the thermoplastic compositions of the invention.

The levels of the NIRF present in the final "tagged" thermoplastic composition may vary considerably depending upon the molar extinction coefficient and the fluorescing efficiency of the added fluorophore. It is generally desirable that the fluorophore be present at the lowest practical level needed to produce a satisfactory fluorescence detection level to avoid minimizing any color problems resulting from the presence of the fluorophore in the thermoplastic and to minimize cost. Normally, with suitable fluorescence efficiency the NIRF is added in the amount of from about 0.5 ppm to about 100 ppm, with about 1 ppm to about 10 ppm being preferred.

Two general routes are available for the synthesis of NIRF compounds of Formula II. Route I involves the reaction of substituted phthalonitriles VI containing one or more leaving groups Z with one or more nucleophiles VII (A. W. Snow and J. R. Griffith, Macromolecules, 1984, 17 (1614–1624), in the presence of a high boiling polar solvent such as N,N-dimethylformamide, N,N-dimethylacetamide, N-methyl-2-pyrrolidinone, tetramethylurea, and hexamethyl-phosphotriamide to give intermediates VIII, which are further reacted by known procedures to give compounds II directly in a one-pot process or to give the isoindoline derivatives IX, which are converted into the desired phthalocyanines II by known processes.

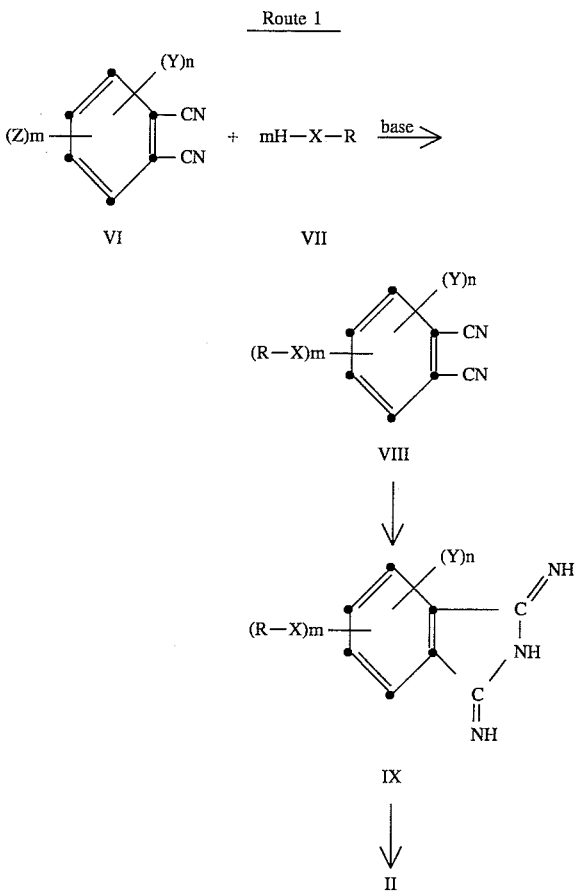

Of course, the starting compounds VI may contain further substitutents which are not replaced by reaction with the nucleophile. Route 2 employs similar reaction conditions, as involved in initial step of Route 1, and makes use of the reactivity of the halogen atoms in polyhalo phthalocyanines X, containing 4–16 halogen atoms attached at peripheral carbon atoms, with nucleophiles VII (UK 1,537,375 and U.S. Pat. No. 4,606,859) to give NIRF compounds II.

Route 2

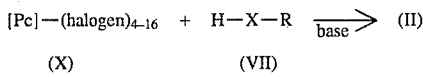

In the above nucleophilic reactions utilized in Routes 1 and 2, the base, or acid binding agent, may be an alkali metal hydroxide, an alkali metal bicarbonate or an alkali metal carbonate. For example, sodium carbonate, potassium carbonate, lithium hydroxide, sodium hydroxide, sodium bicarbonate are suitable bases.

The 2,3-naphthalocyanines of Formula III can be prepared by reacting 2,3-naphthalene-dicarbonitrile compounds XI to give 1,3-diiminobenz[f]-isoindolines XII, which are then converted to the naphthalocyanines of Formulae III by known procedures [J.A.C.S. 1984, 106, 7404–7410; U.S. Pat. No. 5,039,600, incorporated herein by reference; Zn. Obshch. Khim, 1972, 42(3), 696–9 (CA 77: 141469m); Jap. Pat. 61,215,663 (CA 106: 86223s)].

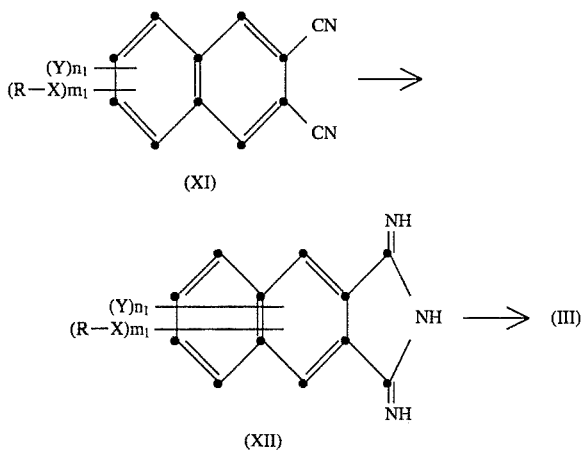

Intermediate compounds XI which contain one or more electron donating groups (—X—R) are conveniently prepared by reacting intermediate 2,3-naphthalene-carbonitriles XIII

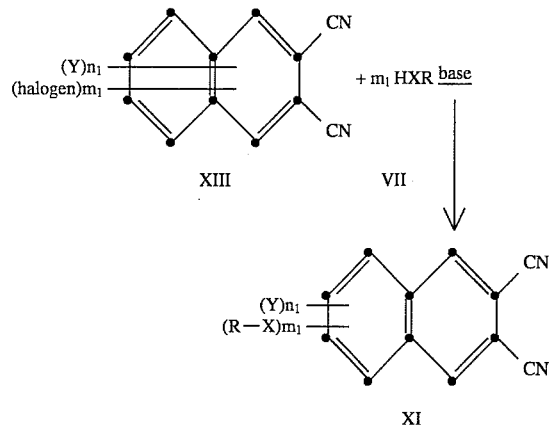

containing replaceable halogens with one or more nucleophiles under reaction conditions which favor nucleophilic displacements (J. Heterocyclic Chem. 1990, Vol. 27, Iss. 7, pp 2219–20).

The squaraines of Formula IV can be prepared by reacting the corresponding unsubstituted and substituted 1,3-dihydro-2-methylene-1,1-dimethyl-1H-benz[e]indoles with squaric acid [S. Cohen, et al., JACS, 81, 3480 (1959)]. The reactions of squaric acid are well known in the art [R. West, editor, *OXOCARBONS*, Academic Press, New York, 1980, pp 185–231; G. Maahs and P. Hagenberg, Angew. Chem. internat. Edit., Vol. 5 (1966), No. 10, p 888; A. H. Schmidt, Synthesis, December 1980, p, 961]. The intermediate 1,3-dihydro-2-methylene-1,1-dimethyl- 1H- benz[e]indoles XIV can be synthesized by known procedures [U.S. Pat. No. 5,030,708, incorporated herein by reference]. The synthetic route is illustrated as follows:

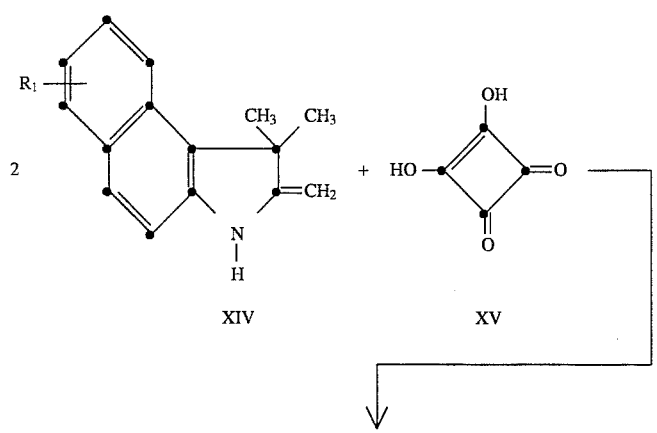

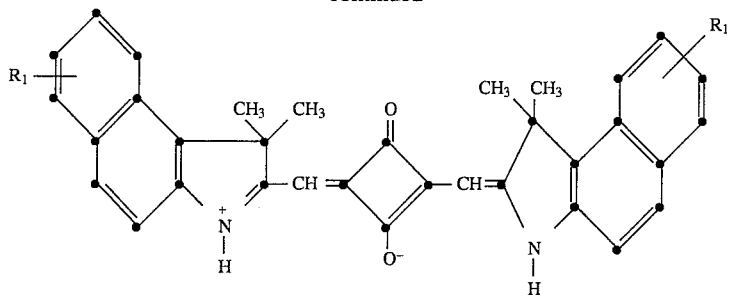

Intermediate 1,3-dihydro-2-methylene-1,1-dimethyl-1H-benz[e] indoles XIV are reacted with squaric acid XV as shown to produce the squaraines. Of course, an unsymmetrical derivative is obtained as one of the components of the mixture prepared by reacting a mixture of two or more different intermediate benz[e]indole compounds XIV with squaric acid.

Thus, as a further aspect of the present invention, there is provide a compound of Formulae II, III, or IV:

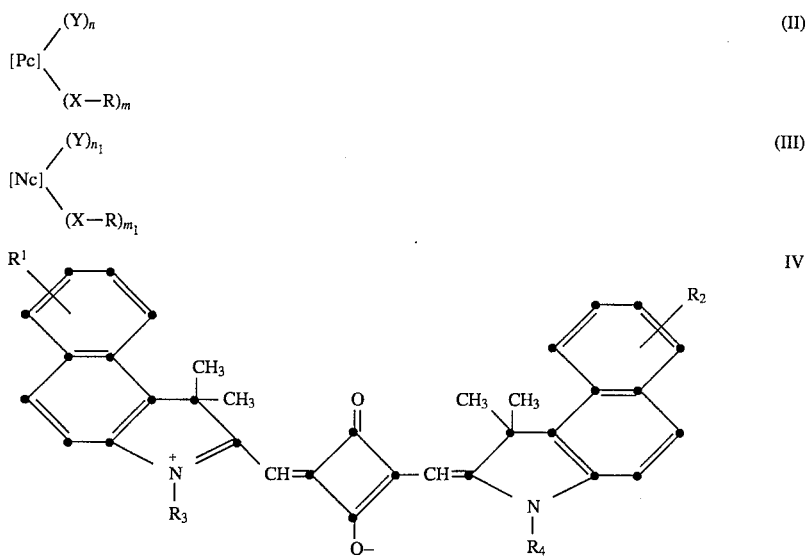

wherein Pc and Nc represent the phthalocyanine and 2,3-naphthalocyanine moieties of Formulae IIa and IIIa,

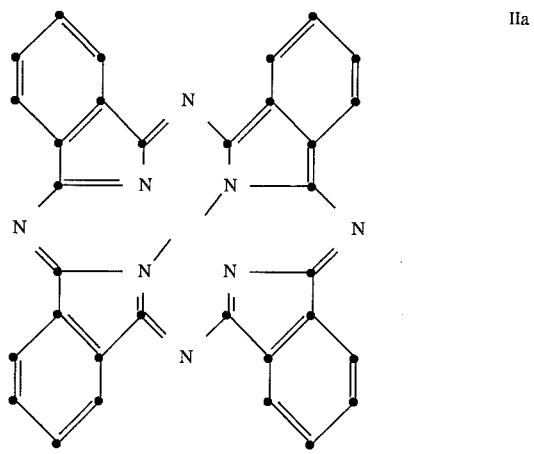

-continued

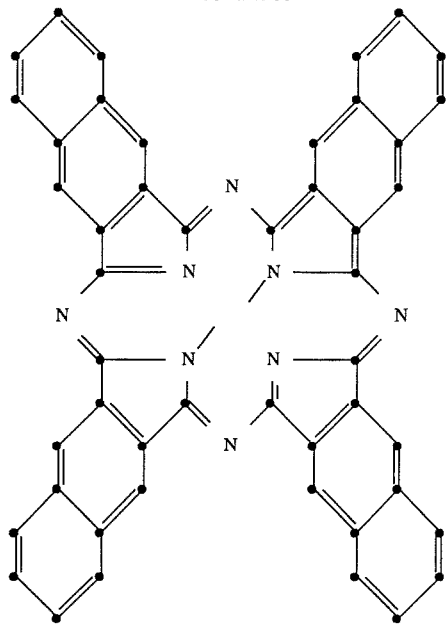

IIIa respectively, covalently bonded to various organometallic groups selected from a list consisting of $AlOR_5$, $AlSR_5$, $Si(OR_6)_2$, $Si(SR_6)_2$, or $Sn(SR_6)_2$, wherein $R_5$ and $R_6$ are aryl or heteroaryl;

X is selected from oxygen, sulfur, selenium, tellurium or N—$R_{10}$, wherein $R_{10}$ is hydrogen, cycloalkyl, alkyl, acyl, alkylsulfonyl, or aryl or $R_{10}$ and R taken together form an aliphatic or aromatic ring with the nitrogen atom to which they are attached;

Y is selected from alkyl, halogen or hydrogen;

R is selected from unsubstituted or substituted alkyl, acyl, alkenyl, alkynyl, $C_3$-$C_8$ cycloalkyl, aryl, heteroaryl, alkylene

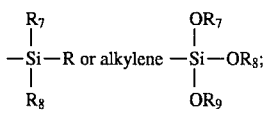

or

—(X—R)$_m$ is alkylsulfonylamino, arylsulfonylamino, or a group selected from the formulae —X($C_2H_4O$)$_z R^1$,

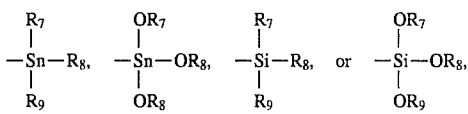

wherein $R^1$ is hydrogen or R as defined above; Z is an integer of from 1–4; or two —(X—R)$_m$ groups can be taken together to form divalent substituents of the formula

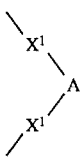

wherein each $X^1$ is independently selected from —O—, —S—, or —N—$R_{10}$ and A is selected from ethylene; propylene; trimethylene; and such groups substituted with $C_1$-$C_4$ alkyl, $C_1$-$C_4$ alkoxy, aryl and cycloalkyl; 1,2-phenylene and 1,2-phenylene containing 1–3 substituents selected from $C_1$-$C_4$ alkyl, $C_1$-$C_4$ alkoxy or halogen;

$R_1$ and $R_2$ are polyester reactive groups;

$R_3$ and $R_4$ are independently selected from hydrogen, lower alkyl, alkenyl or aryl; n is an integer from 0–12; $n_1$ is an integer from 8–24, m is an integer from 4–16; $m_1$ is an integer from 0–16; provided that the sums of n+m and $n_1$+$m_1$ are 16 and 24, respectively, further provided that at least one polyester reactive groups is present.

As a preferred embodiment of this aspect of the present invention, there is provided the above compounds substituted by at least two polyester reactive groups.

As noted above, one apparatus useful for practicing the present invention for identification of the NIRF marker in the polymer described hereinabove is shown in the drawing FIG. 1 wherein like numerals reference like parts. FIG. 1 is a pictorial diagram of the first preferred embodiment of the apparatus useful in the present invention. This arrangement will be understood to be an application of commercially available fluorometers for example currently manufactured by SLM Aminco of Urbana, Ill. This arrangement is for performing the tests of the present invention one at a time. It will be apparent that in using this apparatus, it will be necessary to perform calculations for the concentration ratio of the markers externally. As may be seen from FIG. 1, there is present a light source (1) capable of emitting radiation in the visible and NIR region which illuminates the polymer sample (2) through a wavelength selector (3) e.g., monochromator or interference filter. A wavelength selector (4) and a NIR sensitive photodetector (5) is placed at 90° or less angle. It may be seen from FIG. 1 that light source (1), wavelength selectors (3 & 4) and photodetector (5) are all arranged on two sides of a triangle to minimize scattered light entering the detector. The arrangement of the light source, wavelength selector and detector to minimize scattered light entering the detector is known to those skilled in the art and the routines of obtaining fluorescence signal are not considered novel per se. The light source (1) in FIG. 1 may be replaced with lasers, preferably semiconductor lasers. The output of photodetector (5) is provided to level adjustment amplifier (6), the output of which is provided to an integrated circuit digital multimeter. In the preferred embodiment, digital multimeter (7) is embodied by a computerized unit currently manufactured by SLM Aminco of Urbana, Ill. The output of the digital multimeter is connected to a computer display so as to provide a numeral and graphical indication of the amount of luminous flux at the predetermined wavelength (preferably at the emission maxima) emitted by the substance contained in polymer. It is of course apparent that level adjustment amplifier (6) should be adjusted to provide an output appropriately scaled to suit digital multimeter (7).

Figure 2:
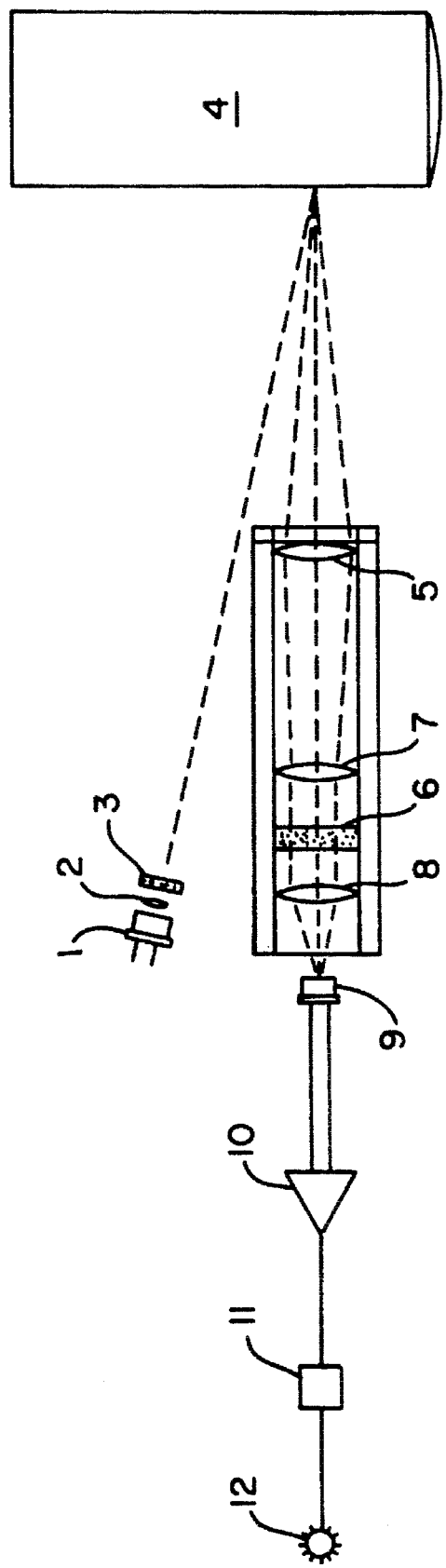
FIG. 2 shows a preferred apparatus useful for practice of the present invention which will be understood to be a specialized arrangement for performing the tests of the present invention. As may be seen from FIG. 2, there is present a laser diode light source (1) capable of emitting radiation in the NIR region which is collimated through a collimating lens (2), and illuminates the container (4) through an optical filter (3). A focusing lens (5) and a beam compressor are placed at 30 degrees or less angle. It may be seen from FIG. 2 that the laser diode light source and the collimating lens are arranged to minimize scattered light from entering the detector. An optical filter (6) is placed between the compressor lenses (7 & 8) to select the wavelength of fluorescence of the tagging molecule which is focused on the photodetector. A current-to-voltage converter is connected to the photo-detector (9) to amplify the detector signal. The arrangement and the electronic circuitry of the current-to-voltage amplifier (10) is widely known and the routines of amplifying and processing the photodetector signal are also well-known. The signal from the current-to-voltage converter circuit is detected by a threshold detector (11). The threshold level of the threshold detector is set at the level required to minimize any interference from untagged containers. The presence of tagged containers in front of the preferred apparatus is indicated by the light-emitting diode (LED) indicator (12).

FIG. 2 shows a preferred embodiment of the apparatus useful for practice of the present invention which will be understood to be a specialized arrangement for performing the tests of the present invention. As may be seen from FIG. 2, there is present a laser diode light source (1) capable of emitting radiation in the NIR region which is collimated through a collimating lense (2), and illuminates the container (4) through an optical filter (3). A focusing lens (5) and a beam compressor are placed at 30 degrees or less angle. It may be seen from FIG. 2 that the laser diode light source and the collimating lens are arranged to minimize scattered light from entering the detector. An optical filter (6) is placed between the compressor lenses (7 & 8) to select the wavelength of fluorescence of the tagging molecule which is focused on the photodetector. A current-to-voltage converter is connected to the photodetector (9) to amplify the detector signal. The arrangement and the electronic circuitry of the current-to-voltage amplifier (10) is widely known and the routines of amplifying and processing the photodetector signal are also well-known. The signal from the current-to-voltage converter circuit is detected by a threshold detector (11). The threshold level of the threshold detector is set at the level required to minimize any interference from untagged containers. The presence of tagged containers in front of the preferred apparatus is indicated by the LED indicator (12). The LED indicator may be replaced with appropriate mechanical or electronic actuators for physical sorting of the containers such as air jets for moving indicated containers from one conveyor to another.

For identification of more than one type of polymer, the use of more than one marker is necessary. In other words, one fluorophore can be used to mark polyesters, another to mark high density polypropylene, another to mark polycarbonates, etc. In these instances, the use of more than one unit of the preferred apparatus as shown in FIG. 2 is necessary. The choice of markers is dependent on their spectral properties, wherein the absorption and fluorescence maxima are sufficiently separated from each other to allow for identification of the individual markers (e.g., about 20 nm or more). The multiplexing and computing apparatus which is programmed to calculate ratios of fluorescence signal of the markers present in the polymer is within the ability of one of ordinary skill in the art.

The following examples illustrate further the practice of the invention.

EXPERIMENTAL SECTION

Example 1

A mixture of methyl 1,1,2-trimethyl-1H-benz[e]-indole-7-carboxylate (tautomer is methyl 1,3-dihydro-2-methylene-1,1-dimethyl-1H-benz [e] indole-7-carboxylate), 2.67 g (0.01M) (see U.S. Pat. No. 5,030,708), squaric acid (0.57 g, 0.005M) and 2-ethoxyethanol (40 g) was heated at reflux under nitrogen for 16 hours. The reaction mixture was cooled with an ice bath and the green solid collected by filtration, washed with isopropanol and dried in air. Recrystallization from 2-ethoxyethanol (20 mL), collection of the solid by filtration, washing of the solid with isopropanol and drying gave the pure product. Mass spectrometry indicated mostly the following structure plus a small amount

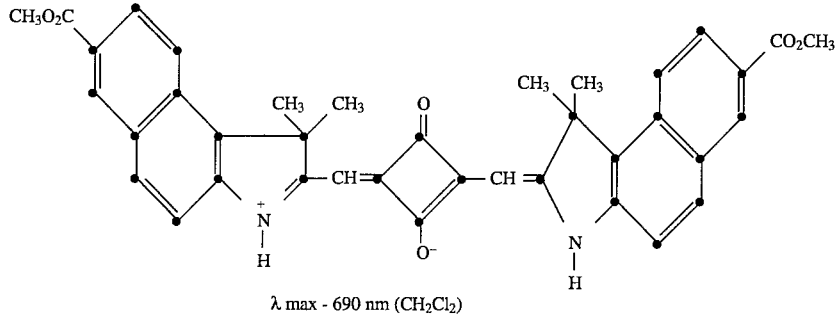

λ max - 690 nm (CH$_2$Cl$_2$)

of the mono 2-ethoxyethyl ester which had been produced by transesterification. In methylene chloride an absorption maximum (λ max) was observed in the visible-near infrared absorption spectrum at 690 nm (ε-214,287).

Example 2

The following materials were placed in a 500 mL three-necked, round-bottom flask:

116.3 g (0.60 mole) dimethyl terephthalate 81.0 g (0.90 mole) 1,4-butanediol 0.0132 g Ti from a n-butanol solution of titanium tetraisopropoxide 0.132 g (2.16×10$^{-4}$ mole) near infrared fluorophore of Example 1

The flask was equipped with a nitrogen inlet, stirrer, vacuum outlet, and condensing flask. The flask and contents were heated in a Belmont metal bath with a nitrogen sweep over the reaction mixture as the temperature was increased to 200° C. and then to 215° C. over 2 hours. Over the next 1.0 hour the temperature was increased to about 230° C. Vacuum was applied until the pressure was reduced to 0.5 mm Hg. The polycondensation was completed by heating the flask and contents at about 230° C. for about 1.0 hour under a pressure of 0.1 to 0.5 mm Hg. The flask was removed from the metal bath and was allowed to cool while the polymer solidified. The resulting pale green polyester, containing about 1000 ppm of the squaraine near infrared fluorophore residue, has an inherent viscosity of 0.44, a weight average molecular weight of 23,367, a number average molecular weight of 15,482, a polydispersity value of 1.51 and a melting temperature of 226° C.

Example 3

TENITE® brand polypropylene P5-029 (Eastman Kodak Company) (9,900 g) was dry blended with 100 g of polymer of Example 2 which had been ground using a Wiley mill.

The materials were compounded and extruded using a Sterling 1.25 inch single-screw extruder at a maximum temperature of about 220° C. to produce pellets, which were then molded into a thin-walled container having a wall thickness of 20–25 mils. The polymer sample, which contains about 10 ppm of the near infrared fluorophore, exhibits strong fluorescence when exposed to light generated by a laser diode source at 672 nm. A maximum at about 712 nm is observed in the emission spectrum.

Example 4

A 300 mL 3-neck round-bottom flask was equipped with a magnetic stirrer, thermometer and gas inlet tube. Methanol (50 mL) was added followed by sodium metal (0.66 g, 0.029 mole) with stirring to facilitate reaction and solution, with a slow nitrogen purge applied. To this solution was added 12.54 g (0.058 mole) of 4-phenoxyphthalonitrile (A. W. Snow and J. R. Griffith, Macromolecules, 1984, 17, 1614–24), followed by additional methanol (50 mL). Anhydrous ammonia was bubbled in under the surface, giving an exotherm to 45° C. and total solution. The ammonia addition was continued until no more starting material was evident by thin-layer chromatography. The solution was clarified by filtering through a pad of Dicalite filter aid which had a small layer of charcoal on it and the filtrate drowned into water. The oily product layer thus produced was washed by decantation with 500 mL portions of water (4–5 times or until pH reached about 7–8). After the final wash water was decanted off, methanol was added to dissolve the product, which crystallized upon stirring overnight at room temperature. After being collected by filtration, the greenish-yellow solid was washed with methylene chloride and dried in air. The yield was 13.75 g, 91.1% of the theoretical yield. Mass spectrometry showed the product to consist largely of the desired 5-phenoxy-1,3-diiminoisoindoline.

Example 5

A mixture of 5-phenoxy-1,3-diiminoisoindoline (3.68 g, 0.016 m) (from Example 4), 1,2,3,4-tetrahydronaphthalene (20 mL) and tri-n-butylamine (10 mL) was stirred under a nitrogen sweep. Aluminum chloride (3.19 g, 0.024 m) was added to give a slurry. After the reaction mixture was heated at about 180° C. for 4 hours, it was allowed to cool to room temperature and diluted with methanol to enhance solubility to facilitate transfer into about 500 mL of ice-water mixture containing 10 mL HCl. The somewhat "greasy" solid product was collected by filtration and washed with dilute HCl. The filter cake was washed on the filter with cyclohexane and finally washed thoroughly with ethyl acetate and dried in air. Mass spectrometry indicated good quality 2(3), 9(10), 16(17), 23(24)-tetraphenoxy—Pc—Al—Cl (Pc=phthalocyanine moiety) having the desired molecular weight of 942 (1.56 g, 41.4 % of the theoretical yield).

Example 6

A portion (110 mg) of the tetraphenoxy-chloro-aluminumphthalocyanine of Example 5 was dissolved in trifluoroacetic acid (10 mL) and allowed to evaporate at room temperature. As evidenced by mass spectrometry, the residual product was mostly 2(3), 9(10), 16(17), 23(24)-tetraphenoxy-Pc-AlOCOCF$_3$, molecular weight 1020. In methylene chloride, absorption maxima were observed at 696 nm ($\epsilon$—126,170), 629 nm ($\epsilon$—26,697), 341 nm ($\epsilon$—58,872) and 292 nm ($\epsilon$—30,600) in the ultraviolet, visible, near-infrared absorption spectra.

Example 7

The following compounds were placed in a 500 mL, single-necked, round-bottom flask:

129.98 g (0.67 mol) dimethyl terephthalate 83.08 g (1.34 mol) ethylene glycol 1.04 mL of a n-butanol solution of acetyltriisopropyl titanate which contained 0.0128 g Ti 0.0013 g (1.27×10$^{-6}$ mol) near infrared fluorophore of Example 6

The flask was equipped with a nitrogen inlet, stirrer, vacuum outlet, and condensing flask. The flask and contents were heated at 200° C. in a Belmont metal bath for 60 minutes, at 210° C. for 75 minutes, and at 230° C. for 50 minutes with a nitrogen sweep over the reaction mixture. The temperature of the bath was increased to 270° C. With a stream of nitrogen bleeding in the system, vacuum was applied slowly at 270° C. over a 10 minute period until the pressure was reduced to 100 mm Hg. The flask and contents were heated at 270° C. under a pressure of 100 mm Hg for 30 minutes. The metal bath temperature was increased to 285° C. and the pressure was reduced to 4.5 mm Hg over a 10 minute period. The flask and contents were heated at 285° C. under a pressure of 4.5 mm Hg for 25 minutes. Then the pressure was reduced to 0.3 mm Hg and polycondensation was continued at 285° C. for 16 minutes. The flask was removed from the metal bath and was allowed to cool while the polymer crystallized. The resulting polymer has an inherent viscosity of 0.55 measured in a 60/40 ratio by weight of phenol/tetrachloroethane at a concentration of 0.5 g per 100 mL. The resulting polymer contains about 10 ppm of the phthalocyanine near infrared fluorescent compound and has a weight average molecular weight of 38,051, a number average molecular weight of 21,078, a polydispersity of 1.80 and a melting temperature of 255° C. The sample was ground in a Wiley mill and a film sample prepared by compression molding of approximately 1 g granules to form a 13-mil thick film using a 2-inch diameter, circular mold at 285° C. and 4500 pounds ram force (4 inch ram) in a Pasadena Hydraulic, Inc. press. The film had a very slight yellowish-green color and when exposed to 672 nm wavelength light from a laser diode source exhibited a strong fluorescence with a maximum intensity of emitted light at wavelength of approximately 700 nm.

Example 8

A reaction mixture of tetraphenoxy-chloroaluminum phthalocyanine (0.94 g) of Example 5, dimethyl-3-hydroxyisophthalate (0.24 g) and pyridine (20 g) was heated at reflux for 24 hours and allowed to cool to room temperature. Added isopropanol (20 mL) and then precipitated, by the addition of water, the phthalocyanine product, which was collected by filtration, washed with water and dried in air (yield—0.90 g). In methylene chloride, absorption maxima were observed at 696 nm (104,585), 626 nm (32,882) and 343 nm (64,090) in the ultraviolet, visible and near infrared absorption spectra.

Example 9

The near infrared fluorophore (0.0013 g) of Example 8 was added to dimethyl terephthalate (129.98 g), 0.67 mole) and ethylene glycol (83.08 g, 1.34 mole). Titanium catalyst (1.04 mL of a n-butanol containing 0.0128 g of Ti as acetyl triisopropyl titanate) was added and the polymerization reaction carried out under the conditions described in Example 7. The resulting very pale green polymer contains approximately 10 ppm of the near infrared fluorophore and has an inherent viscosity of 0.50, a weight average molecular weight of 34,310, a number average molecular weight of 22,247, a polydispersity of 1.54 and a melting temperature of 253° C. A 13-mil thick film was prepared as in Example 7. When exposed to 672 nm light from a laser diode source the film exhibited a strong fluorescence with a maximum intensity of emitted light at approximately 700 nm.

Example 10

The following compounds were placed in a 500 mL three-neck, round bottom flask:

116.38 g (0.60 mole) dimethyl terephthalate 81.00 g (0.90 mole) 2-methyl-1,3-propanediol 0.0128 g Ti from a n-butanol solution of titanium tetraisopropoxide The flask was equipped with a nitrogen inlet, stirrer, vacuum outlet and condensing flask. The flask and contents were heated in a Belmont metal bath with a nitrogen sweep over the reaction mixture as the temperature was increased to 200° C. and then to 230° C. over 1.5 hours. The reaction temperature was increased to about 250° C. over 1 hour and the near infrared fluorophore of Example 1 (0.0396 g, 6.47×10$^{-5}$ mole) was added. A vacuum was applied until the pressure was reduced to about 0.5 mm Hg and heating continued at 250° C. and at 0.1–0.5 mm Hg for about 10 minutes. The flask was removed from the metal bath and allowed to cool while the polymer solidified. The very light green polymer which contained about 300 ppm of the NIRF has an inherent viscosity of 0.21, a weight average molecular weight of 12,437, a number average molecular weight of 7,993, a polydispersity of 1.55 and no melting temperature by differential scanning calorimetry (DSC) analysis.

Example 11

TENITE® brand polypropylene P5-029 (Eastman Kodak Company) (9,900 g) was dry blended with 100 g of polymer of Example 9, which had been previously ground using a Wiley mill, and the mixture compounded and extruded at a maximum temperature of about 220° C. to produce pellets, which were then molded into a thin-walled container having a wall thickness of about 20–25 mils. The polymer sample, which contains about 3 ppm of the NIRF, exhibits strong fluorescence when exposed to light generated by a laser diode source at 672 nm. A maximum at about 708 nm was observed in the emission spectrum.

Example 12

A mixture of 5-phenoxy-1,3-diiminoisoindoline (3.68 g, 0.016 mole), silicon tetrachloride (4.0 g, 0.024 mole) 1,2,3,4-tetrahydronaphthalene (20 mL) and tri-n-butylamine (10 mL) was heated under nitrogen at about 200° C. for 40 minutes, allowed to stir overnight at room temperature and reheated to 180° C. and held for about 2.0 hours. After cooling to room temperature, the reaction mixture was diluted with 30 mL of methanol, filtered, and the collected solid washed with methanol and dried in air (yield—2.71 g, 69.3% of the theoretical yield). Mass spectrometry supported the structure: 2(3), 9(10), 16(17), 23(24)-tetraphenoxy —Pc—Si—(Cl)$_2$.

Example 13

A mixture of the tetraphenoxy-dichlorosiliconphthalocyanine (0.49 g) of Example 12, methyl 4-hydroxybenzoate (0.16 g) and pyridine (5 g) was heated at reflux for 3 hours under nitrogen. To the cooled reaction mixture were added isopropanol (20 mL) and then water (20 mL) with stirring. The product was collected by filtration, washed with water and dried in air. Mass spectrometry supports the structure: 2(3), 9(10), 16(17), 23(24)-tetraphenoxy- Pc—Si—(OC$_6$H$_4$-4-CO$_2$CH$_3$)$_2$.

Example 14

The near infrared fluorophore (0.0013 g, 1.07×10$^{-6}$ mole) of Example 13 was added to ethylene glycol (83.08 g, 1.34 mole) and dimethyl terephthalate (129.98 g, 0.67 mole) and the polymerization reaction carried out as described in Example 7 in the presence of 0.0128 g titanium catalyst. The resulting pale green polymer contains approximately 10 ppm of the NIRF and has an inherent viscosity of 0.82, a melting temperature of 252° C. by DSC, a weight average molecular weight of 59,274, a number average molecular weight of 31,578 and a polydispersity of 1.88. The polymer was ground in a Wiley mill and a film having a thickness of about 13 mils was prepared as in Example 7. When the film was exposed to 672 nm wavelength light from a laser diode source, significant fluorescence with a maximum intensity of emitted light at wavelength of approximately 698 nm was observed.

Example 15

A mixture of silicon phthalocyanine dichloride (0.2 g) was dissolved in trifluoroacetic acid (10 mL) and the reaction mixture allowed to stand in a hood in an evaporating dish until all the the excess trifluoroacetic acid had evaporated. Absorption maxima were observed at 691 nm (ε—168,645), 659 nm (ε—21,596), 622 nm (ε—24,789), 356 (ε—50,090) and 334 nm (44,608) in the ultraviolet-visible-near infrared absorption spectra. The product was assumed to be silicon phthalocyanine trifluroacetate (Pc—Si(OCOCF$_3$)$_2$.

Example 16

The NIRF compound of Example 15 (0.0013 g, 1.70×10$^{-6}$ mole) was added to dimethyl terephthalate (129.98 g) and ethylene glycol (83.08 g, 1.34 mole) and the polymerization reaction carried out as in Example 7 in the presence of 0.0128 g Ti (from a n-butanol solution of acetyl-triisopropyl titanate). The pale blue green polymer contains approximately 10 ppm of the NIRF and has an inherent viscosity of 0.52, a weight average molecular weight of 35,646, a number average molecular weight of 19,737, a polydispersity of 1.81 and a melting temperature of 256° C. The polymer was ground in a Wiley mill and a film having a thickness of about 13 mils was prepared as in Example 7. When the film was exposed to 672 nm wavelength light from a laser diode source, significant fluorescence over the wavelength range of about 675 to about 780 nm was emitted with apparent emission maxima at about 687 nm and 755 nm.

Example 17

The following compounds were placed in a 500 mL three-neck, round bottom flask:

116.40 g (0.60 mole) dimethyl terephthalate 81.00 g (0.90 mole) 2-methyl-1,3-propanediol 0.0133 g Ti from a n-butanol solution of titanium tetraisopropoxide 1.60 g (2.07×10$^{-3}$ mole) Nc—Si—(OH)$_2$ (B. L. Wheeler, et al., J.A.C.S. 1984, 106, 7404–7410; Nc represents naphtaholocyanine)

The flask was equipped with a nitrogen inlet, stirrer, vacuum outlet and condensing flask. The flask and contents were heated in a Belmont metal bath with a nitrogen sweep over the reaction mixture and the temperature was increased to about 200° C. and then to 230° C. over about 1.5 hour. The reaction temperature was increased to about 250° C. over 1 hour and then vacuum was applied and heating continued at about 250° C. for about 1.0 hour at 0.1 to 0.5 mm Hg. The flask was removed from the metal bath and allowed to cool while the polymer solidified. The very pale yellowish-green polymer contains about 1.0% by weight of the NIRF and has an inherent viscosity of 0.44, a weight average molecular weight of 25,053, a number average molecular weight of 13,710, a polydispersity of 1.83 and a melting temperature of about 157° C. The polymer was ground in a Wiley mill.

Example 18

Poly(ethylene terephthalate) (6,000 g) having an inherent viscosity of about 0.71, which had been ground using a Wiley mill to a particle size of about 2 mm, was blended with 1.0 g of the polymer containing the NIRF of Example 17. This blend was vacuum dried at about 110° C. for 16 hours and then compounded and extruded using a Sterling 1.25 inch single-screw extruder at a maximum temperature of 270° C. to produce pellets, which were molded into a thin-walled container having a wall thickness of about 13 mils. The polymer sample contains about 1–2 ppm of the near infrared fluorophore. When a sample of the side wall is exposed to infrared light in a near infrared spectrophotometer set on a wavelength of 780 nm, a broad band fluorescence is observed with a peak at about 795 nm.

Example 19

A reaction mixture of Nc—Si(OH)$_2$ (1.5 g) (J.A.C.S. 1984, 106, 7404–7410), pyridine (150 mL) and chloro dimethylphenylsilane (10 mL) was heated at reflux for 5 hours and then allowed to cool. Some insolubles were filtered off and the filtrate stripped on a rotary evaporator under vacuum. Pentane (300 mL) was added to the residue to produce a solid upon stirring which was collected by filtration, washed with 50/50 acetone/water, then with pentane and dried in air. The solid (1.9 g) was reslurried in hot pentane (300 mL) and filtered hot. The solid thus obtained was washed with pentane and air dried (yield—1.5 g). Mass spectrometry supported the following structure

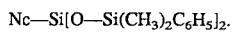

Nc—Si[O—Si(CH$_3$)$_2$C$_6$H$_5$]$_2$.

Example 20

The following materials were placed in a 500-mL three-necked, round-bottom flask:

116.40 g (0.60 mole) dimethyl terephthalate 81.00 g (0.90 mole) 1,4-butanediol 0.0132 g Ti from a n-butanol solution of titanium tetraisopropoxide 0.132 g (1.27×10$^{-4}$ mole) NIRF of Example 19

The flask was equipped with a nitrogen inlet, stirrer, vacuum outlet, and condensing flask. The flask and contents were heated in a Belmont metal bath with a nitrogen sweep over the reaction mixture as the temperature was increased to 200° C. and then to 230° C. over 2 hours. Over the next 1.0 hour the temperature was increased to about 250° C. Vacuum was applied until the pressure was reduced to 0.5 mm Hg. The polycondensation was completed by heating the flask and contents at about 250° C. for about 1.0 hour under a pressure of 0.1 to 0.5 mm Hg. The flask was removed from the metal bath and was allowed to cool while the polymer solidified. The resulting polyester, containing about 1,000 ppm of the NIRF of Example 19, has an inherent viscosity of 0.79, a weight average molecular weight of 43,573, a number average molecular weight of 25,230, a polydispersity value of 1.73 and a melting temperature of 228° C. The sample was ground in a Wiley mill.

Example 21

Poly(ethylene terephthalate) (6,000 g) having an inherent viscosity of about 0.71, which had been ground using a Wiley mill to a particle size of about 2 mm, was dry blended with 10.0 g of the polymer composition of Example 20, which contained about 1,000 ppm of the NIRF. This blend was dried in a vacuum oven at 110° C. for 16 hours and then compounded and extruded into pellets using a Sterling 1.25 inch compounding single-screw extruder at about 280° C. The pellets were molded into a thin-walled bottle having a side wall thickness of about 13 mils and containing about 1–2 ppm of the NIRF. When a sample of the side wall is exposed to infrared light in a near infrared spectrophotometer set on a wavelength of 780 nm, a broad band fluorescence is observed with a peak at about 800 nm.

Example 22

Tolylene 2,4-diisocyanate (8.7 g, 0.05M) was added dropwise to a solution of N,N-dimethylformamide (100 mL) which contained 4.50 g (0.05M) and 13.4 mg (1.0×10$^{-5}$M) of Nc—Si(OH)$_{-2}$ (B. Wheeler, et al., J.A.C.S. 1984, 106, 7404–7410). After the addition was completed the reaction mixture was heated at 80–85° C. with stirring for 0.5 hours and then allowed to cool to room temperature.

Methanol (5.0 mL) was added and the solution was then drowned into water containing 5 mL of saturated salt solution. The essentially white polyurethane polymer was collected by filtration, washed with 2.0 L of water and then dried in air. The yield was 12.2 g of polymer which contains about 0.1% by weight of the NIRF and which has an inherent viscosity of 0.14, a weight average molecular weight of 8,253, a number average molecular weight of 6,083 and a polydispersity of 1.35. A sample of the polymer when dissolved in N,N-dimethylformamide showed a maximum absorption (λ max) at 775 nm in the near infrared absorption spectrum, with another less intense absorption band having a maximum absorption at about 690 nm.

Additional examples of compounds having Formulae II, III and IV are presented in Tables 3, 4 and 2, respectively.

TABLE 1

EXEMPLARY —X—R Groups

| —X—R | —X—R |
|---|---|
| —OCH$_3$ | (structure: —S—C(=S)—N-fused benzothiazole) |
| —OC$_4$H$_9$-n | (structure: —S—C(=N)—thiazole ring) |
| —OC(CH$_3$)$_3$ | (structure: —S—C(=S)—N=N—CH$_3$ thiadiazole) |
| —OC$_{12}$H$_{25}$-n | (structure: —S—C(=N)—N(C$_2$H$_4$OH)—N=CH triazole) |
| —SCH$_3$ | (structure: —S—C(=O)—N-fused benzoxazole) |
| —SC$_2$H$_4$OH | (structure: —S—C(=NH)—N-fused benzimidazole) |
| —SC$_8$H$_{17}$-n | (structure: —S—C(=S)—N-fused benzothiazole with —OCH$_3$) |
| —OCH$_2$CH(C$_2$H$_5$)C$_4$H$_9$-n | (structure: —S—C(=O)—N=N— with —CO$_2$CH$_3$, oxadiazole) |
| —OCH$_2$CH=CH$_2$ | (structure: —S—phenyl—OCH$_3$) |
| —OCH$_2$CH=CH—CH$_3$ | (structure: —Te—phenyl—CH$_3$) |

TABLE 1-continued

EXEMPLARY —X—R Groups

| —X—R | —X—R |
|---|---|
| —SCH$_2$C$_6$H$_5$ | —Se—C$_6$H$_5$ (phenyl) |
| —SCH$_2$CH(OH)CH$_2$OH | —OCH$_2$C$_6$H$_4$-4-COOH |
| —OCH$_2$C≡CH | —OC$_6$H$_4$-4-CH$_2$COOH |
| —N(C$_2$H$_5$)$_2$ | —OCH$_2$CH$_2$CO$_2$CH$_3$ |
| —NHC$_6$H$_5$ | —OCH$_2$CH$_2$OCOCH$_3$ |
| —N(CH$_3$)C$_6$H$_5$ | —O—C$_6$F$_5$ |
| —N(C$_2$H$_4$OH)$_2$ | —OC$_6$H$_4$-4-Cl |
| —NHC$_6$H$_{11}$ | —O—naphthyl |

| —X—R | —X—R |
|---|---|
| —N(piperidinyl) | —O—naphthyl |
| —OC$_6$H$_5$ | —O(CH$_2$CH$_2$O)$_2$H |
| —OC$_6$H$_4$-4-COOH | —S(CH$_2$CH$_2$O)$_2$H |
| —SC$_6$H$_4$-4-COOH | —O(CH$_2$CH$_2$O)$_4$H |
| —OC$_6$H$_3$-3,5-diCOOH | —O(CH$_2$CH$_2$O)$_3$CH$_3$ |
| —OC$_6$H$_3$-diCO$_2$CH$_3$ | —O(CH$_2$CH$_2$O)$_2$C$_6$H$_5$ |
| —SC$_6$H$_4$-2-COOH | —NH(CH$_2$CH$_2$O)$_2$H |
| —SC$_6$H$_4$-3-CO$_2$CH$_3$ | |
| —OC$_6$H$_4$-4-C$_2$H$_4$OH | |
| —OC$_6$H$_4$-4-OC$_2$H$_4$OH | |

TABLE 2

| Ex. No. | R$_1$ | R$_2$ | R$_3$ | R$_4$ |
|---|---|---|---|---|
| 23 | 7-CO$_2$CH$_3$ | 7-CO$_2$CH$_3$ | CH$_3$ | CH$_3$ |
| 24 | 7-CO$_2$C$_2$H$_5$ | 7-CO$_2$C$_2$H$_5$ | C$_6$H$_5$ | C$_6$H$_5$ |
| 25 | 7-CO$_2$C$_6$H$_5$ | 7-CO$_2$C$_6$H$_5$ | C$_6$H$_4$-4-CH$_3$ | C$_6$H$_4$-4-CH$_3$ |
| 26 | 7-CONH$_2$ | 7-CONH$_2$ | H | H |
| 27 | 7-CONHC$_2$H$_4$OH | 7-CONHC$_2$H$_4$OH | H | H |
| 28 | 7-CON(CH$_3$)C$_2$H$_4$OH | 7-CON(CH$_3$)C$_2$H$_4$OH | CH$_3$ | CH$_3$ |
| 29 | 7-CON(C$_2$H$_4$OH)$_2$ | 7-CON(C$_2$H$_4$OH)$_2$ | H | H |
| 30 | 7-CONHC$_6$H$_{11}$ | 7-CONHC$_6$H$_{11}$ | C$_4$H$_9$-n | C$_4$H$_9$-n |
| 31 | 7-CONHC$_6$H$_5$ | 7-CONHC$_6$H$_5$ | H | H |
| 32 | 7-CONHCH$_2$C$_6$H$_{10}$-4-CH$_2$OH | 7-CONHCH$_2$C$_6$H$_{10}$-4-CH$_2$OH | CH$_3$ | CH$_3$ |
| 33 | 7-CONHC$_6$H$_4$-4-CO$_2$CH$_3$ | 7-CONHC$_6$H$_4$-4-CO$_2$CH$_3$ | H | H |
| 34 | 7-SO$_2$NH$_2$ | 7-SO$_2$NH$_2$ | H | H |
| 35 | 7-SO$_2$N(C$_2$H$_5$)$_2$ | 7-SO$_2$N(C$_2$H$_5$)$_2$ | CH$_3$ | CH$_3$ |
| 36 | 7-SO$_2$N(CH$_3$)C$_6$H$_{11}$ | 7-SO$_2$N(CH$_3$)C$_6$H$_{11}$ | CH$_3$ | CH$_3$ |
| 37 | 7-SO$_2$N(piperidinyl) | 7-SO$_2$N(piperidinyl) | H | H |
| 38 | 7-SO$_2$N(morpholinyl) | 7-SO$_2$N(morpholinyl) | H | H |
| 39 | 7-SO$_2$N(piperidinyl) | 7-SO$_2$N(piperidinyl) | H | H |
| 40 | 7-SO$_2$NHC$_2$H$_4$OH | 7-SO$_2$NHC$_2$H$_4$OH | C$_6$H$_5$ | C$_6$H$_5$ |
| 41 | 7-SO$_2$N(CH$_3$)C$_2$H$_4$OH | 7-SO$_2$N(CH$_3$)C$_2$H$_4$OH | H | H |
| 42 | 7-SO$_2$NHC$_6$H$_4$-3-CO$_2$CH$_3$ | 7-SO$_2$NHC$_6$H$_4$-3-CO$_2$CH$_4$ | H | H |

TABLE 2-continued

| Ex. No. | $R_1$ | $R_2$ | $R_3$ | $R_4$ |
|---|---|---|---|---|
| 43 | 7-SO$_2$NHC$_6$H$_4$-4-C$_2$H$_4$OH | 7-SO$_2$NHC$_6$H$_4$-4-C$_2$H$_4$OH | H | H |
| 44 | 7-SO$_2$NHC$_6$H$_4$-3-CH$_2$OH | 7-SO$_2$NHC$_6$H$_4$-3-CH$_2$OH | CH$_3$ | CH$_3$ |
| 45 | 7-SO$_2$NHC$_6$H$_{11}$ | 7-SO$_2$NHC$_6$H$_{11}$ | CH$_2$CH=CH$_2$ | CH$_2$CH=CH$_2$ |
| 46 | 7-CH$_3$ | 7-CH$_3$ | H | H |
| 47 | 7-OC$_6$H$_5$ | 7-OC$_6$H$_5$ | H | H |
| 48 | 7-OC$_2$H$_4$OH | 7-OC$_2$H$_4$OH | H | H |
| 49 | 7-SC$_2$H$_5$ | 7-SC$_2$H$_5$ | H | H |
| 50 | 7-SC$_6$H$_5$ | 7-S-C$_6$H$_5$ | H | H |
| 51 | 7-Br | 7-Br | CH$_3$ | CH$_3$ |
| 52 | 8-OH | 8-OH | H | H |
| 53 | 8-OCH$_3$ | 8-OCH$_3$ | H | H |
| 54 | 8-OCOCH$_3$ | 8-OCOCH$_3$ | H | H |
| 55 | H | H | H | H |
| 56 | 7-COOH | 7-COOH | H | H |
| 57 | 7-CO$_2$CH$_3$ | H | H | CH$_3$ |
| 58 | 7-CO$_2$CH$_3$ | 7-SO$_2$NHC$_2$H$_4$OH | H | H |
| 59 | H | 7-SO$_2$N(C$_2$H$_4$OH)$_2$ | H | H |
| 60 | 7-CO$_2$CH$_3$ | 7-CO$_2$CH$_3$ | C$_6$H$_5$ | CH$_3$ |
| 61 | 7-SO$_2$C$_6$H$_5$ | 7-SO$_2$C$_6$H$_5$ | H | H |
| 62 | 7-SO$_2$CH$_3$ | 7-SO$_2$CH$_3$ | H | H |
| 63 | 7-SO$_2$(CH$_2$)$_4$OH | 7-SO$_2$(CH$_2$)$_4$OH | H | H |
| 64 | 7-SO$_2$C$_6$H$_4$-3-CO$_2$CH$_3$ | 7-SO$_2$C$_6$H$_4$-3-CO$_2$CH$_3$ | H | H |

TABLE 3

PHTHALOCYANINE COMPOUNDS
(Pc = PHTHALOCYANINE NUCLEUS)

| No. | COMPOUND |
|---|---|
| 65 | 3(4), 9(10), 16(17), 23(24)-Tetraphenoxy-PcH$_2$ |
| 66 | 3(4), 9(10), 16(17), 23(24)-Tetraphenoxy-PcAlOH |
| 67 | 3(4), 9(10), 16(17), 23(24)-Tetraphenoxy-PcAl—OC$_6$H$_4$-4-CO$_2$CH$_3$ |
| 68 | 3(4), 9(10), 16(17), 23(24)-Tetraphenoxy-PcAl-SC$_6$H$_4$-2-CO$_2$CH$_3$ |
| 69 | 3(4), 9(10), 16(17), 23(24)-Tetraphenoxy-PcAl-S-C$_2$H$_4$OH |
| 70 | 3(4), 9(10), 16(17), 23(24)-Tetraphenoxy-PcCu |
| 71 | 3(4), 9(10), 16(17), 23(24)-Tetraphenoxy-PcCa |
| 72 | 3(4), 9(10), 16(17), 23(24)-Tetraphenoxy-PcVO |
| 73 | 3(4), 9(10), 16(17), 23(24)-Tetraphenoxy-PcInCl |
| 74 | 3(4), 9(10), 16(17), 23(24)-Tetraphenoxy-PcCrF |
| 75 | 3(4), 9(10), 16(17), 23(24)-Tetra-(4-methoxyphenoxy)-PcAlOCOCF$_3$ |
| 76 | 3(4), 9(10), 16(17), 23(24)-Tetra-(4-methoxyphenoxy)-PcNi |
| 77 | 3(4), 9(10), 16(17), 23(24)-Tetra-(4-methoxyphenoxy)-Sn |
| 78 | 3(4), 9(10), 16(17), 23(24)-Tetra-(4-methoxyphenoxy)-PcSnCl$_2$ |
| 79 | 3(4), 9(10), 16(17), 23(24)-Tetra-(4-methoxyphenoxy)-PcSn(OCOCH$_3$)$_2$ |
| 80 | 3(4), 9(10), 16(17), 23(24)-Tetra-(4-methoxyphenoxy)-PcSiF$_2$ |
| 81 | 3(4), 9(10), 16(17), 23(24)-Tetra-(4-methoxyphenoxy)-PcCo |
| 82 | 3(4), 9(10), 16(17), 23(24)-Tetra-(4-t-butylphenylthio)-PcH$_2$ |
| 83 | 3(4), 9(10), 16(17), 23(24)-Tetra-(4-t-butylphenylthio)-PcCu |
| 84 | 3(4), 9(10), 16(17), 23(24)-Tetra-(4-t-butylphenylthio)-PcAlCl |
| 85 | 3(4), 9(10), 16(17), 23(24)-Tetra-(4-t-butylphenylthio)-PcAlOCOCF$_3$ |
| 86 | 3(4), 9(10), 16(17), 23(24)-Tetra-(4-t-butylphenylthio)-PcGe |
| 87 | 3(4), 9(10), 16(17), 23(24)-Tetra-(4-t-butylphenylthio)-PcGa |
| 88 | 3(4), 9(10), 16(17), 23(24)-Tetra-(4-t-butylphenoxy)-PcSiCl$_2$ |
| 89 | 3(4), 9(10), 16(17), 23(24)-Tetra-(4-t-butylphenoxy)-PcSiOH |
| 90 | 3(4), 9(10), 16(17), 23(24)-Tetra-(4-t-butylphenoxy)-PcSi(OC$_2$H$_4$OH)$_2$ |
| 91 | 3(4), 9(10), 16(17), 23(24)-Tetra-(4-t-butylphenoxy)-PcSi(OC$_4$H$_9$-n)$_2$ |
| 92 | 3(4), 9(10), 16(17), 23(24)-Tetra-(4-t-butylphenoxy)-PcZn |
| 93 | 3(4), 9(10), 16(17), 23(24)-Tetra-(4-t-butylphenoxy)-Pc-Mg |
| 94 | 3(4), 9(10), 16(17), 23(24)-Tetra-(4-t-butylphenoxy)-PcMn |
| 95 | 3(4), 9(10), 16(17), 23(24)-Tetra-(4-t-butylphenoxy)-PcPt |
| 96 | 3(4), 9(10), 16(17), 23(24)-Tetra-(4-t-butylphenoxy)-PcPd |
| 97 | 3(4), 9(10), 16(17), 23(24)-Tetra-(4-t-butylphenoxy)-PcPb |
| 98 | 3(4), 9(10), 16(17), 23(24)-Tetra-(4-t-butylphenoxy)-PcSi(OCOCH$_3$)$_2$ |
| 99 | 3(4), 9(10), 16(17), 23(24)-Tetra-(4-t-butylphenoxy)-PcSiF$_2$ |
| 100 | 3(4), 9(10), 16(17), 23(24)-Tetra-(2-hydroxyethoxy)-PcAlOH |

TABLE 3-continued

PHTHALOCYANINE COMPOUNDS
(Pc = PHTHALOCYANINE NUCLEUS)

| No. | COMPOUND |
| --- | --- |
| 101 | 3(4), 9(10), 16(17), 23(24)-Tetra-(2-hydroxyethylthio)-Pc AlOCOCF$_3$ |
| 102 | 3(4), 9(10), 16(17), 23(24)-Tetra-(4-carbomethoxyphenoxy)-PcSiCl$_2$ |
| 103 | 3(4), 9(10), 16(17), 23(24)-Tetra-(2-carboxyphenylthio)-PcSi(OH)$_2$ |
| 104 | 3(4), 9(10), 16(17), 23(24)-Tetra-(3-carbomethoxyphenylthio)-PcH$_2$ |
| 105 | 3(4), 9(10), 16(17), 23(24)-Tetra-n-butoxy-PcVO |
| 106 | 3(4), 9(10), 16(17), 23(24)-Tetraallyloxy-PcSn(OCOCF$_3$)$_2$ |
| 107 | 3(4), 9(10), 16(17), 23(24)-Tetrabenzylthio-PcCu |
| 108 | 3(4), 9(10), 16(17), 23(24)-Tetrabenzyloxy-PcZn |
| 109 | 3(4), 9(10), 16(17), 23(24)-Tetracyclohexyloxy-PcSi[OC(C$_6$H$_5$)$_3$]$_2$ |
| 110 | 3(4), 9(10), 16(17), 23(24)-Tetrabenzothiazol-2-ylthio-PcH$_2$ |
| 111 | 3(4), 9(10), 16(17), 23(24)-Tetrabenzothiazol-2-ylthio-PcAlCl |
| 112 | 3(4), 9(10), 16(17), 23(24)-Tetrabenzoxazol-2-ylthio-PcAlOCCOCF$_3$ |
| 113 | 3(4), 9(10), 16(17), 23(24)-Tetra(5-methyl-1,3,4-thiadiazol-2-ylthio)-PcH$_2$ |
| 114 | 3(4), 9(10), 16(17), 23(24)-Tetra-2-pyridylthio-PcSi(OC$_6$H$_5$)$_2$ |
| 115 | 3(4), 9(10), 16(17), 23(24)-Tetraphenyltelluro-PcCu |
| 116 | 3(4), 9(10), 16(17), 23(24)-Tetraphenylseleno-PcNi |
| 117 | 3(4), 9(10), 16(17), 23(24)-Tetra-n-octylthio-PcSi(OC$_6$H$_4$-4-F)$_2$ |
| 118 | 3(4), 9(10), 16(17), 23(24)-Tetra-(2-naphthylthio)-PcAlOH |
| 119 | 3(4), 9(10), 16(17), 23(24)-Tetradiethylamino-PcH$_2$ |
| 120 | 3(4), 9(10), 16(17), 23(24)-Tetrapiperidino-PcSn(OCOCF$_3$)$_2$ |
| 121 | 3(4), 9(10), 16(17), 23(24)-Tetratriazol-3-ylthio-PcSiCl$_2$ |
| 122 | 3(4), 9(10), 16(17), 23(24)-Tetratriazol-3-ylthio-PcAl—OCOCF$_3$ |
| 123 | 3(4), 9(10), 16(17), 23(24)-Tetraanilino-Pc-Cu |
| 124 | 3(4), 9(10), 16(17), 23(24)-Tetra(4-methoxyanilino)-Pc-SnCl$_2$ |
| 125 | 3(4), 9(10), 16(17), 23(24)-Tetra(4-dodecyloxyphenoxy)-PcIn-Cl |
| 126 | 3(4), 9(10), 16(17), 23(24)-Tetra(2-naphthyloxy)-PcH$_2$ |
| 127 | 3(4), 9(10), 16(17), 23(24)-Tetra(4-carbomethoxyphenylthio)-Pc-AlOH |
| 128 | 1,4,8,11,15,18,22,25-Octamethoxy-2,3,9,10,16,17,23,24-Octachloro-PcSi(OH)$_2$ |
| 129 | 1,4,8,11,15,18,22,25-Octamethoxy-2,3,9,10,16,17,23,24-Octachloro-PcAl—Cl |
| 130 | 1,4,8,11,15,18,22,25-Octamethoxy-2,3,9,10,16,17,23,24-Octachloro-PcAlOCOCF$_3$ |
| 131 | 1,4,8,11,15,18,22,25-Octamethoxy-2,3,9,10,16,17,23,24-Octachloro-PcCu |
| 132 | 1,4,8,11,15,18,22,25-Octamethoxy-2,3,9,10,16,17,23,24-Octachloro-PcVO |
| 133 | Hexadecachloro-PcAlOH |
| 134 | Hexadecaanilino-PcH$_2$ |
| 135 | Hexadeca(4-methylphenylthio)-PcSi(OC$_6$F$_5$)$_2$ |
| 136 | 1,4,8,11,15,18,22,25-Octaphenoxy-PcSiF$_2$ |
| 137 | 1,4,8,11,15,18,22,25-Octaphenylthio-PcSi[O—Si(CH$_3$)$_2$C$_6$H$_5$]$_2$ |
| 138 | 1,4,8,11,15,18,22,25-Octa-n-hexyloxyphenoxy-PcH$_2$ |
| 139 | 1,4,8,11,15,18,22,25-Octa-(4-t-butylphenylthio)-PcCu |
| 140 | 1,4,8,11,15,18,22,25-Octa-(4-methylthiophenylthio)PcFe |
| 141 | 2,3,9,10,16,17,23,24-Octachloro-Pc-Al—OH |
| 142 | 2,3,9,10,16,17,23,24-Octabromo-Pc-AlOCOCF$_3$ |
| 143 | 2,3,9,10,16,17,23,24-Octafluoro-Pc-SiCl$_2$ |
| 144 | 2,3,9,10,16,17,23,24-Octaphenylthio-PcSi(OC$_6$H$_5$)$_2$ |
| 145 | 2,3,9,10,16,17,23,24-Octa(2-hydroxyethoxy)PcSi[OC$_6$H$_4$-4-COOH]$_2$ |
| 146 | 2,3,9,10,16,17,23,24-Octa(2-hydroxyethylthio)PcSi(OCOCF$_3$)$_2$ |
| 147 | 2,3,9,10,16,17,23,24-Octa(2-butylphenylthio)-PcCu |
| 148 | 2,3,9,10,16,17,23,24-Octa(t-butoxyphenoxy)-PcH$_2$ |
| 149 | 2,3,9,10,16,17,23,24-Octabenzothiazol-2-ylthio-PcAlOH |
| 150 | 1,4,8,11,15,18,22,25-Octa(3-methylbutoxy)-2,3,9,10,16,17,23,24-octaphenylthio-PcAlOH |
| 151 | 1,4,8,11,15,18,22,25-Octa(3-methylbutoxy)-2,3,9,10,16,17,23,24-octaphenoxy-PcSi(OH)$_2$ |
| 152 | 1,4,8,11,15,18,22,25-Octa(3-methylbutoxy)-2,3,9,10,16,17,23,24-octa-n-butylthio-PcH$_2$ |
| 153 | 1,4,8,11,15,18,22,25-Octafluoro(3-methylbutoxy)-2,3,9,10,16,17,23,24-octa-4(t-butylphenylthio)PcCu |
| 154 | 1,4,8,11,15,18,22,25-Octafluoro-2,3,9,10,16,17,23,24-octaphenylthio-PcAlOC$_6$H$_4$-4-CO$_2$CH$_3$ |
| 155 | 1,4,8,11,15,18,22,25-Octafluoro-2,3,9,10,16,17,23,24-octaphenylthio-PcVO |

TABLE 4

NAPHTALOCYANINE COMPOUNDS
(Nc = NAPHTHALOCYANINE NUCLEUS)

| No. | COMPOUND |
| --- | --- |
| 156 | 2(3), 11(12), 20(21), 29(30) Tetra-t-butyl-NcH$_2$ |
| 157 | 2(3), 11(12), 20(21), 29(30) Tetra-t-butyl-NcCu |
| 158 | 2(3), 11(12), 20(21), 29(30) Tetra-t-butyl-NcSi(OH)$_2$ |

TABLE 4-continued

NAPHTALOCYANINE COMPOUNDS
(Nc = NAPHTHALOCYANINE NUCLEUS)

| No. | COMPOUND |
|---|---|
| 159 | 2(3), 11(12), 20(21), 29(30) Tetra-t-butyl-NcVO |
| 160 | 2(3), 11(12), 20(21), 29(30) Tetra-t-butyl-NcAlOH |
| 161 | 2(3), 11(12), 20(21), 29(30) Tetra-t-butyl-NcAlOCOCF$_3$ |
| 162 | 2(3), 11(12), 20(21), 29(30) Tetra-t-butyl-NcZn |
| 163 | 2(3), 11(12), 20(21), 29(30) Tetra-t-butyl-NcSnCl$_2$ |
| 164 | 2(3), 11(12), 20(21), 29(30) Tetra-t-butyl-NcCo |
| 165 | 2(3), 11(12), 20(21), 29(30) Tetra-t-butyl-NcCa |
| 166 | 2(3), 11(12), 20(21), 29(30) Tetra-t-butyl-NcPd |
| 167 | 2(3), 11(12), 20(21), 29(30) Tetra-t-butyl-NcAlOC$_6$H$_4$-4-COOH |
| 168 | 2(3), 11(12), 20(21), 29(30) Tetra-t-butyl-NcAlOC$_6$H$_3$-3,5-diCO$_2$CH$_3$ |
| 169 | 2(3), 11(12), 20(21), 29(30) Tetra-t-butyl-NcSi(OC$_6$H$_4$-4-CO$_2$CH$_3$)$_2$ |
| 170 | 2(3), 11(12), 20(21), 29(30) Tetra-t-butyl-NcSn(OCOCH$_3$)$_2$ |
| 171 | 2(3), 11(12), 20(21), 29(30) Tetramethyl-NcH$_2$ |
| 172 | 2(3), 11(12), 20(21), 29(30) Tetramethoxy-NcAlOH |
| 173 | 2(3), 11(12), 20(21), 29(30) Tetramethylthio-NcAlOCCOCF$_3$ |
| 174 | NCVO |
| 175 | NcInCl |
| 176 | NcZn |
| 177 | Nc(SiOCOCF$_3$)$_2$ |
| 178 | NcMg |
| 179 | 2(3), 11(12), 20(21), 29(30) Tetra-n-butoxy-NcH$_2$ |
| 180 | 2(3), 11(12), 20(21), 29(30) Tetra-n-butoxy-NcVO |
| 181 | 2(3), 11(12), 20(21), 29(30) Tetra-n-butoxy-NcSi(OH)$_2$ |
| 182 | 2(3), 11(12), 20(21), 29(30) Tetra-n-butoxy-NcSi[OSi(C$_6$H$_5$)$_3$]$_2$ |
| 183 | 2(3), 11(12), 20(21), 29(30) Tetra-n-butoxy-NcSn[OCOCH$_3$)$_2$ |
| 184 | 2(3), 11(12), 20(21), 29(30) Tetra-n-butoxy-NcZn |
| 185 | 2(3), 11(12), 20(21), 29(30) Tetra-n-butoxy-NcMg |
| 186 | 2(3), 11(12), 20(21), 29(30) Tetradodecyloxy-NcSi(OH)$_2$ |
| 187 | 2(3), 11(12), 20(21), 29(30) Tetrabenzothiazol-2-yl-thio-NcAlOH |
| 188 | 2(3), 11(12), 20(21), 29(30) Tetrabenzimidazol-2-ylthio-NCAlOCOCF$_3$ |
| 189 | 2(3), 11(12), 20(21), 29(30) Tetraphenylseleno-NcSnCl$_2$ |
| 190 | 2(3), 11(12), 20(21), 29(30) Tetraphenyltelluro-NcSiCl$_2$ |
| 191 | 2(3), 11(12), 20(21), 29(30) Tetraanilino-NcSi(OH)$_2$ |
| 192 | 2(3), 11(12), 20(21), 29(30) Tetra-(2-naphthyloxy)-NcCSi(OCOCF$_3$)$_2$ |
| 193 | 2(3), 11(12), 20(21), 29(30) Tetra-(2-naphthylthio)-NcSi(OCOCH$_3$)$_2$ |
| 194 | 2(3), 11(12), 20(21), 29(30) Tetraallyloxy-Nc-Sn(OCOCH$_3$)$_2$ |
| 195 | 2(3), 11(12), 20(21), 29(30) Tetrapropargyloxy-NC-Si(OH)$_2$ |
| 196 | 2(3), 11(12), 20(21), 29(30) Tetracyclohexyloxy-NC-Si[OC$_6$H$_3$-3,5-diCO$_2$CH$_3$]$_2$ |
| 197 | 2(3), 11(12), 20(21), 29(30) Tetra(2-phenoxyethoxy)-Nc-AlOH |
| 198 | 2(3), 11(12), 20(21), 29(30) Tetra(2-phenylethoxy)-Nc-VO |
| 199 | 2(3), 11(12), 20(21), 29(30) Tetrabenzyloxy-Nc-InCl |
| 200 | 2(3), 11(12), 20(21), 29(30) Tetrapiperidino-Nc-Cu |
| 201 | 5,9,14,18,23,27,32,36-Octamethoxy-NcSi(OH)$_2$ |
| 202 | 5,9,14,18,23,27,32,36-Octa-n-butoxy-NcSi(OCCOCF$_3$)$_2$ |
| 203 | 5,9,14,18,23,27,32,36-Octaphenoxy-NcMg |
| 204 | 5,9,14,18,23,27,32,36-Octaallyloxy-NcAlOC$_6$H$_4$-4-CO$_2$CH$_3$ |
| 205 | 5,9,14,18,23,27,32,36-Octaethoxy-NcVO |
| 206 | 2(3), 11(12), 20(21), 29(30) - Tetrachloro-NcH$_2$ |
| 207 | 2(3), 11(12), 20(21), 29(30) - Tetrabromo-NcH$_2$ |
| 208 | 2,3,11,12,20,21,29,30-Octabromo-NcZn |
| 209 | 2,3,11,12,20,21,29,30-Octaphenoxy-NcAlOH |
| 210 | 2,3,11,12,20,21,29,30-Octaphenylthio-NcSi(OH)$_2$ |
| 211 | 2,3,11,12,20,21,29,30-Octabenzothiazol-2-ylthio-NcSi(OCOCF$_3$)$_2$ |
| 212 | 2,3,11,12,20,21,29,30-Octabenzoxazol-2-ylthio-NcVo |
| 213 | 2,3,11,12,20,21,29,30-Octatriazol-3-ylthio-NcCu |
| 214 | 2,3,11,12,20,21,29,30-Octa(4-t-butoxyphenoxy)NcAlOH |
| 215 | 2,3,11,12,20,21,29,30-Octa(4-methoxyphenylthio)NcSi(OH)$_2$ |
| 216 | 2,3,11,12,20,21,29,30-Octa(2-ethylhexoxy)-NcSi(OH)$_2$ |
| 217 | 2,3,11,12,20,21,29,30-Octa(2-hydroxyethoxy)-NcAlCl |
| 218 | 2,3,11,12,20,21,29,30-Octa(2-hydroxyethylthio)-NcSi(OH)$_2$ |
| 219 | 2,3,11,12,20,21,29,30-Octa(4-hydroxybutylthio)-NcH$_2$ |
| 220 | 2,3,11,12,20,21,29,30-Octamethyl-NcAlOH |
| 221 | 2,3,11,12,20,21,29,30-Octa-p-t-butylphenylthio-Nc-Si(OH)$_2$ |
| 222 | 2(3), 11(12), 20(21), 29(30)-Tetra diethylamino-NcAlOH |
| 223 | 2(3), 11(12), 20(21), 29(30)-Tetra morpholino-NcAlOCOCF$_3$ |
| 224 | 2(3), 11(12), 20(21), 29(30)-Tetra-O(C$_2$H$_4$O)$_2$CH$_3$-Nc-Si(OH)$_2$ |
| 225 | 2(3), 11(12), 20(21), 29(30)-Tetra-O(C$_2$H$_4$O)$_2$CH$_3$-Nc-Si(OH)$_2$ |
| 226 | 2(3), 11(12), 20(21), 29(30)-tetra [(CH$_3$)$_3$-Si-CH$_2$S]-Nc-Si[OSi(C$_4$H$_9$)$_3$]$_2$ |
| 227 | 2(3), 11(12), 20(21), 29(30)-tetra [(C$_2$H$_5$)$_3$-Si-(CH$_2$)$_2$S]-Nc-Si[OSi(CH$_3$)$_3$]$_2$ |
| 228 | 2(3), 11(12), 20(21), 29(30)-tetra [(C$_6$H$_{13}$)$_3$-Si-CH$_2$-S]-Nc-Si[OSi(OCH$_3$)$_3$]$_2$ |
| 229 | 2(3), 11(12), 20(21), 29(30)-tetra [(CH$_3$O)$_3$-Si-(CH$_2$)$_3$-S]-Nc- |

TABLE 4-continued

NAPHTALOCYANINE COMPOUNDS
(Nc = NAPHTHALOCYANINE NUCLEUS)

| No. | COMPOUND |
|---|---|
| | Ge[OSi($C_2H_5$)$_3$]$_2$ |
| 230 | 2(3), 11(12), 20(21), 29(30)-tetra [($C_6H_5O$)$_3$-Si-$CH_2$-S]-Nc-Ge[OSi(OCH$_3$)$_3$]$_2$ |
| 231 | 2(3), 11(12), 20(21), 29(30)-tetra [($CH_3$)$_3$-Si-$CH_2CH_2$-O]-Nc-Si(OH)$_2$] |
| 232 | 2(3), 11(12), 20(21), 29(30)-tetra [($CH_3$)$_3$-SiC(Cl)$_2CH_2$S]-Nc-Ge[OSi(CH$_3$)$_3$]$_2$ |
| 233 | 2(3), 11(12), 20(21), 29(30)-tetra [($C_6H_5$)$_{3-SiCH2}$O]-Nc-Ge(OCOCF$_3$)$_2$ |
| 234 | 2(3), 11(12), 20(21), 29(30)-tetra [($CH_3$)$_3$-Si-$CH_2$S]-Nc-Sn[OSi-($C_2H_5$)$_3$]$_2$ |
| 235 | 2(3), 11(12), 20(21), 29(30)-tetra [($CH_3$)$_3$-Si-$CH_2$S]-Nc-Sn[OC$_{18}H_{37}$)$_2$ |
| 236 | 2(3), 11(12), 20(21), 29(30)-tetra [($CH_3$)$_2C_6H_5$Si-($CH_2$)$_4$O]-Nc-AlOH |
| 237 | 2,3,11,12,20,21,29,30-octa [($CH_3$)$_3$Si-$CH_2$S]-Nc-Si(OH)$_2$ |

We claim:

1. A method for detecting and separating thermoplastic containers, said containers comprising a thermoplastic material having admixed therein or copolymerized therein a compound or residue having detectible fluorescence when exposed to near infrared radiation, which comprises the following steps:

(a) exposure of a mixture of thermoplastic containers to near infrared radiation having wavelengths of about 670–2,500 nm, with the provision that at least one of said thermoplastic container compositions has admixed therein or copolymerized therein one or more near infrared tagging compounds or copolymerized residues having substantial near infrared absorbance and which is (are) present in sufficient quantity to impart fluorescence when exposed to radiation having wavelengths of about 670–2,500 nm, provided by light sources;

(b) detection of the emitted (fluorescent) light via near infrared light detection means; and (c) separating the fluorescing containers from the non-fluorescing containers or containers flourescing at a detectibly different wavelength or wavelengths by mechanical means;

wherein the near infrared fluorescing compound or residue thereof is selected from the classes of phathalocyanines, naphthalocyanines and squaraines and correspond to Formulae II, III and IV:

$$\begin{array}{c} (Y)_n \\ (Pc) \\ (X-R)_m \end{array} \quad (II)$$

$$\begin{array}{c} (Y)_{n_1} \\ (Nc) \\ (X-R)_{m_1} \end{array} \quad (III)$$

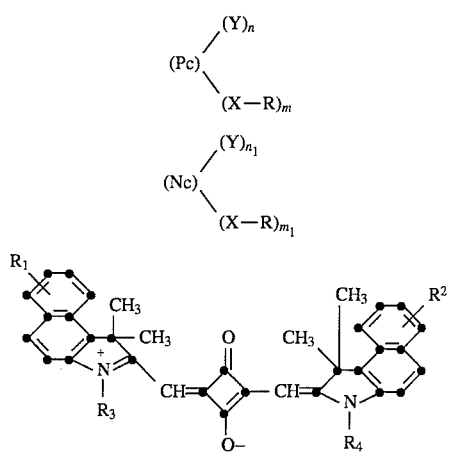

IV wherein Pc and Nc represent the phthalocyanine and 2,3-naphthalocyanine moieties of Formulae IIa and IIIa,

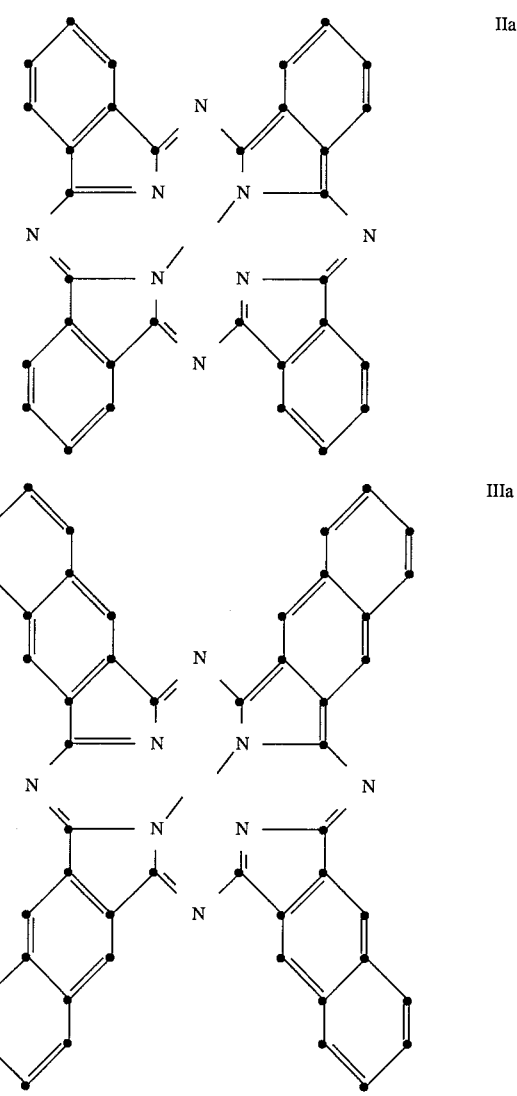

respectively, covalently bonded to hydrogen or to various metals, halometals, organometallic groups, and oxymetals selected from the group consisting of AlCl, AlBr, AlF, AlOH, AlOR$_5$, AlSR$_5$, Ca, Co, CrF, Cu, Fe, Ge, Ga, InCl, Mg, Mn, Ni, Pb, Pt, Pd, SiCl$_2$, SiF$_2$, SnCl$_2$, Sn(OR$_6$)$_2$, Si(OR$_6$)$_2$, Sn(SR$_6$)$_2$, Si(SR$_6$)$_2$, Sn, TiO, VO and Zn, wherein $R_5$ and $R_6$ are selected from hydrogen, alkyl, aryl, lower alkanoyl, trifluoroacetyl or groups of the formulae

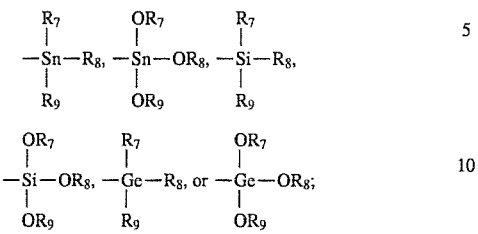

$R_7$, $R_8$ and $R_9$ are independently selected from alkyl, phenyl or phenyl substituted with lower alkyl, lower alkoxy or halogen;

X is selected from oxygen, sulfur, selenium, tellurium or a group of the formula $-N-R_{10}$, wherein $R_{10}$ is hydrogen, cycloalkyl, alkyl, acyl, alkylsulfonyl, or aryl or $R_{10}$ and R taken together form an aliphatic or aromatic ring with the nitrogen atom to which they are attached;

Y is selected from alkyl, halogen or hydrogen;

R is selected from unsubstituted alkyl or substituted alkyl selected from the group consisting of alkyls containing 1–12 carbon atoms and containing as substituents 1 or 2 groups selected from hydroxy, halogen, carboxy, cyano, $C_1-C_4$ alkoxy, aryl, $C_1-C_4$ alkylthio, arylthio, aryloxy, $C_1-C_4$ alkoxycarbonyl, or $C_1-C_4$ alkanoyloxy, alkenyl, alkynyl, $C_3-C_8$ cycloalkyl, aryl, heteroaryl,

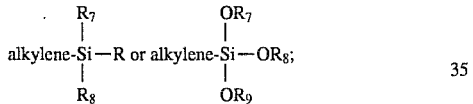

or $-(X-R)_m$ is alkylsulfonylamino, arylsulfonylamino, or a group selected from the formulae $-X(C_2H_4O)_zR^1$

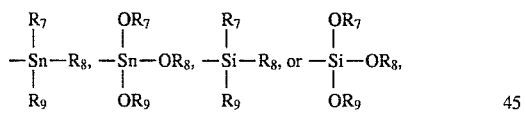

wherein $R^1$ is hydrogen or R as defined above; Z is an integer of from 1–4;

or two $-(X-R)_m$ groups can be taken together to form divalent substituents of the formula

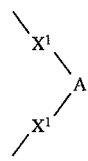

wherein each $X^1$ is independently selected from $-O-$, $-S-$, or $-N-R_{10}$ and A is selected from ethylene; propylene; trimethylene; and such groups substituted with $C_1-C_4$ alkyl, $C_1-C_4$ alkoxy, aryl and cycloalkyl; 1,2-phenylene and 1,2-phenylene containing 1–3 substituents selected from $C_1-C_4$ alkyl, $C_1-C_4$ alkoxy or halogen;

$R_1$ and $R_2$ are independently selected from hydrogen, lower alkyl, lower alkoxy, halogen, aryloxy, lower alkylthio, arylthio, lower alkylsulfonyl; arylsulfonyl; lower alkylsulfonylamino, arylsulfonylamino, cycloalkylsulfonylamino, carboxy, unsubstituted carbamoyl and substituted carbamoyl selected from the group consisting of a radicals having the formula $-CONR_{12}R_{13}$, wherein $R_{12}$ and $R_{13}$ are selected from unsubstituted or substituted alkyl, alkenyl, alkynyl as defined above, cycloalkyl, aryl, or heteroaryl, and unsubstituted sulfamoyl and substituted sulfamoyl selected from the group consisting of radicals having the formula $-SO_2NR_{12}R_{13}$, wherein $R_{12}$ and $R_{13}$ are as defined above, lower alkoxycarbonyl, hydroxy or lower alkanoyloxy,

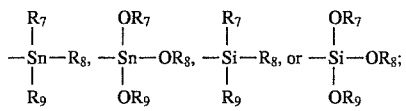

$R_3$ and $R_4$ are independently selected from hydrogen, lower alkyl, alkenyl or aryl; n is an integer from 0–12; $n_1$ is an integer from 0–24, m is an integer from 4–16; $m_1$ is an integer from 0–16; provided that the sums of n+m and $n_1+m_1$ are 16 and 24, respectively.

* * * * *